(12) United States Patent
Palle et al.

(10) Patent No.: US 8,507,508 B2
(45) Date of Patent: Aug. 13, 2013

(54) SOLID FORMS OF PEMETREXED

(75) Inventors: Raghavendracharyulu Venkata Palle, Hyderabad (IN); Sekhar Munaswamy Nariyam, Hyderabad (IN); Vijay Bhailalbhai Patel, Hyderabad (IN); Raghupati Rama Subrahmanyam Vinjamuri, Hyderabad (IN); Surya Narayana Devarakonda, Hyderabad (IN); Sesha Reddy Yarraguntla, Hyderabad (IN); Vamsi Krishna Mudapaka, Khammam (IN); Venu Nalivela, Warangal (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 517 days.

(21) Appl. No.: 12/593,966

(22) PCT Filed: Apr. 4, 2008

(86) PCT No.: PCT/US2008/059344
§ 371 (c)(1),
(2), (4) Date: Sep. 30, 2009

(87) PCT Pub. No.: WO2008/124485
PCT Pub. Date: Oct. 16, 2008

(65) Prior Publication Data
US 2010/0063072 A1    Mar. 11, 2010

Related U.S. Application Data

(60) Provisional application No. 60/979,245, filed on Oct. 11, 2007.

(30) Foreign Application Priority Data

Apr. 3, 2007 (IN) .............................. 704/CHE/2007

(51) Int. Cl.
*A01N 43/90* (2006.01)
*A61K 31/519* (2006.01)
*C07D 487/00* (2006.01)

(52) U.S. Cl.
USPC ......................................... 514/265.1; 544/280

(58) Field of Classification Search
USPC ...................... 514/265.1; 544/280; 585/833
See application file for complete search history.

(56) References Cited

U.S. PATENT DOCUMENTS

| 5,344,932 A | 9/1994 | Taylor |
| 6,013,828 A * | 1/2000 | Kjell et al. ...................... 560/11 |
| 2008/0045711 A1 | 2/2008 | Busolli et al. |

FOREIGN PATENT DOCUMENTS

| EP | 1027887 A2 * | 8/2000 |
| WO | 01/14379 A2 | 3/2001 |
| WO | 01/62760 A2 | 8/2001 |
| WO | 2008/021405 A1 | 2/2008 |
| WO | 2008/021411 A2 | 2/2008 |

OTHER PUBLICATIONS

Lien et. al., and Ripple, Remington's Pharmaceutical Sciences, 1985, Mack Publishing Co. 17th ed., p. 185; p. 1585.*
C. J. Barnett, et al., "A Practical Synthesis of Multitargeted Antifolate LY231514," Journal of Organic Process Research & Development, vol. 3, pp. 184, 1999.

* cited by examiner

*Primary Examiner* — Sreeni Padmanabhan
*Assistant Examiner* — Sarah Pihonak
(74) *Attorney, Agent, or Firm* — Pergament Gilman & Cepeda LLP; Milagros A. Cepeda; Edward D. Pergament

(57) ABSTRACT

There is provided polymorphs and amorphous form of pemetrexed or its pharmaceutical acceptable salts and process for making thereof.

27 Claims, 19 Drawing Sheets

SOLID FORMS OF PEMETREXED

TECHNICAL FIELD

The present patent application relates to solid forms of pemetrexed and its salts and processes for preparing it. The application also relates to amorphous pemetrexed disodium salt and a process for preparation thereof.

BACKGROUND

Pemetrexed disodium is chemically described as L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate, represented by the chemical structure of Formula (I).

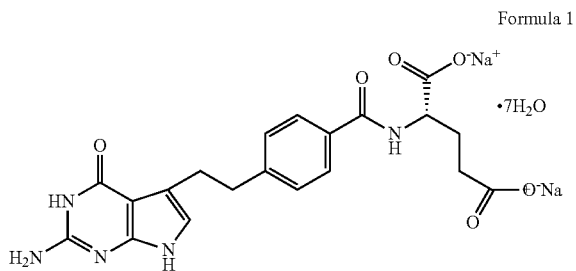

Formula 1

Pemetrexed is an anti-folate anti-neoplastic agent that exerts its action by disrupting folate-dependent metabolic processes essential for cell replication. It is believed to work by inhibiting three enzymes that are required in purine and pyrimidine biosynthesis—thymidylate synthase (TS), dihydrofolate reductase (DHFR), and glycinamide ribonucleotide formyl transferase (GARFT). Pemetrexed is available in the market under the brand name ALIMTA®.

Taylor et al., in U.S. Pat. No. 5,344,932 describe pemetrexed, its related compounds and pharmaceutically acceptable cation.

Chelius et al., in WO 01/14379 A2 disclose pemetrexed disodium crystalline hydrate Form I and process for preparation thereof.

Chelius et al., in WO 01/62760 disclose pemetrexed disodium heptahydrate crystalline Form II and process for the preparation thereof.

Journal of Organic Process Research & Development, Volume 3, 1999, page 184 describes a process for the preparation of pemetrexed diacid.

Busolli et al., in WO2008021411 disclose process for preparation of pharmaceutically acceptable salt of pemetrexed diacid.

Busolli et al., in WO2008021405A1 disclose seven crystalline forms of pemetrexed diacid designated as Form A, B, C, D, E, F, & G and processes for preparation thereof.

There remains a continuing need for new solid forms of pemetrexed disodium and diacid that are sufficiently stable, and the processes of preparation amenable to scale up to production quantities.

SUMMARY

In one aspect, there is provided a compound, which is an amorphous form of disodium salt of pemetrexed. Various embodiments and variants are provided.

In another aspect, there is provided a composition that includes disodium salt of pemetrexed as a solid, wherein at least 50% by weight of the solid disodium salt of pemetrexed is an amorphous form of disodium salt of pemetrexed. Various embodiments and variants are provided.

In another aspect, there is provided a compound, which is a crystalline form of disodium salt of pemetrexed having an X-ray diffraction pattern, expressed in terms of 2 theta angles and obtained with a diffractometer equipped with a copper K α-radiation source, wherein said X-ray powder diffraction pattern includes five or more peaks selected from the group consisting of peaks with 2 theta angles of 4.0±0.2, 17.3±0.2, 18.0±0.2, 19.5±0.2, 20.4±0.2, 21.0±0.2, 29.0±0.2 and 43.3±0.2.

In yet another aspect, there is provided a solid dispersion of disodium salt of pemetrexed which includes i) disodium salt of pemetrexed in an amorphous form; and ii) a pharmaceutically acceptable carrier.

In yet another aspect, there is provided a process for preparing amorphous pemetrexed disodium, including:
  i) providing a solution of pemetrexed disodium in a solvent; and
  ii) removing the solvent.

In yet another aspect, there is provided a process for making a solid, which is a mixture of amorphous and crystalline forms of disodium salt of pemetrexed, the process including:
  i) providing a solution of disodium salt of pemetrexed in water;
  ii) adding an organic hydrocarbon solvent which is capable of forming an azeotropic mixture with water; and
  iii) carrying out an azeotropic distillation until a solid is obtained.

In yet another aspect, there is provided a compound, which is Form A of pemetrexed diacid having X-ray powder diffraction pattern (XRPD) with peaks at about 5.8, 12.4, 18.3, 18.6, 19.6, 20.4, 24.5, 24.9, 25.8, 28.9, 29.2, 29.6, and 32.8, ±0.2 degrees 2θ.

In yet another aspect, there is provided a process for preparing a crystalline form A of pemetrexed diacid, comprising the steps of:
  a) providing a solution of pemetrexed diacid in ethanol;
  b) cooling the mass to cause precipitation of a solid; and
  c) isolating the precipitated solid, which is the crystalline form A of pemetrexed diacid.

In yet another aspect, there is provided a compound which is Form B of pemetrexed diacid having X-ray powder diffraction pattern (XRPD) with peaks at about 5.7, 12.1, 12.3, 17.7, 18.4, 20.2, 22.2, 22.5, 22.7, 24.7, 25.6, 25.8, 26.6, 28.2, 30.3, 31.3, and 31.8, ±0.2 degrees 2θ.

In yet another aspect, there is provided a process for making a crystalline form B of pemetrexed diacid comprising:
  a) providing a solution of pemetrexed diacid in isopropyl alcohol;
  b) cooling the mass to cause precipitation of a solid; and
  c) isolating the precipitated solid, which is the crystalline form B of pemetrexed diacid.

DETAILED DESCRIPTION

Figure 1:
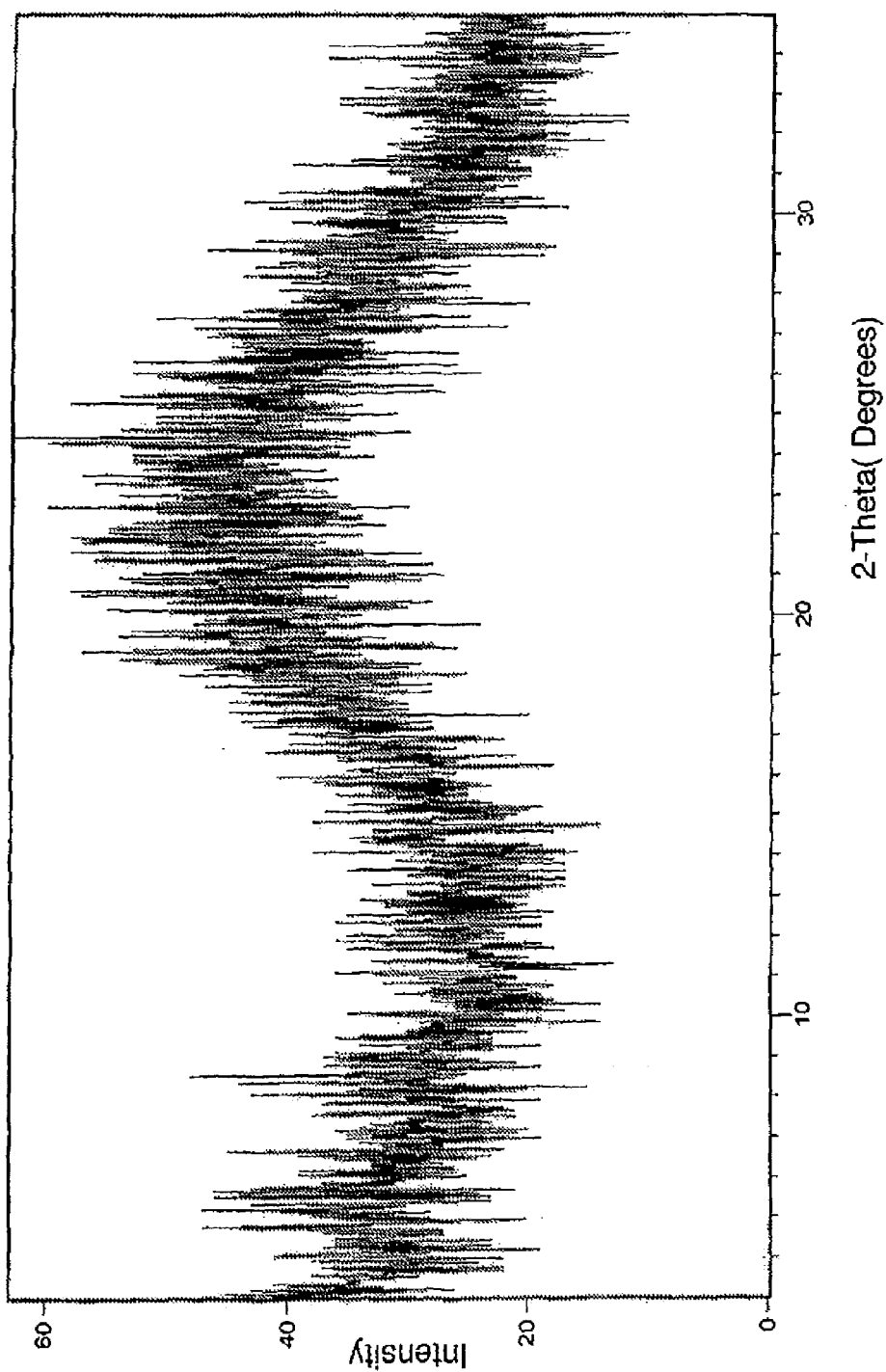
FIG. 1 shows an illustrative example of X-ray powder diffraction pattern of an amorphous form of disodium salt of pemetrexed prepared according to Example 1.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Unless stated to the contrary, any use of the words such as "including," "containing," "comprising," "having" and the like, means "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

For purposes of the present invention, the following terms are defined below.

"Pharmaceutically acceptable" means that which is useful in preparing a pharmaceutical product that is generally non-toxic and is not biologically undesirable and includes that which is acceptable for veterinary use and/or human pharmaceutical use.

The term "compound" is used to refer to a molecular entity of defined chemical structure.

The term "composition" includes, but is not limited to, a powder, a suspension, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds. As used with respect to an active pharmaceutical ingredient, the term "composition" may define a mixture of different solid forms of the same compound.

The term "pharmaceutical composition" is intended to encompass a product that includes the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions described herein encompass any composition made by admixing the active ingredient, additional active ingredient(s), and pharmaceutically acceptable excipients.

The term "excipient" means a component of a pharmaceutical product that is not the active ingredient, such as filler, diluent, carrier, and so on. The excipients that are useful in preparing a pharmaceutical composition are preferably generally safe, non-toxic and neither biologically nor otherwise undesirable, and are acceptable for veterinary use as well as human pharmaceutical use. A "pharmaceutically acceptable excipient" as used in the specification and claims includes both one and more than one such excipient.

When referring to a chemical reaction or a process, the terms "treating", "contacting" and "reacting" are used interchangeably herein and refer to adding or mixing two or more reagents under appropriate conditions to produce the indicated and/or the desired product. It should be appreciated that the reaction, which produces the indicated and/or the desired product, may not necessarily result directly from the combination of two reagents, which were initially added, i.e., there may be one or more intermediates which are produced in the mixture which ultimately leads to the formation of the indicated and/or the desired product. Also, the term "isolating" is used to indicate separation of the compound being isolated regardless of the purity of the isolated compound from any unwanted substance which presents with the compound as a mixture. Thus, degree of the purity of the isolated or separated compound does not affect the status of "isolating".

The term "water content" is used herein to refer to the amount of water present in the solid, in % terms with respect to the weight of the solid, as measured by traditional techniques for determination of water in solids, such as the Karl Fisher test.

The term "solid dispersion" denotes a homogeneous solid containing at least two components of different chemical identity, which components are intimately mixed with one another at a molecular level. For example, such solid dispersion is obtained when two components are present as solute in a liquid solution in a solvent, and obtained as a residue upon solvent evaporation.

The term "solvent" defines any liquid medium in which component(s) is/are dissolved, including an individual solvent or a mixture of solvents.

A single compound may give rise to a variety of solids having distinct physical properties. Different solid forms of the same drug may exhibit different properties, including characteristics that have functional implications with respect to their use as active ingredients of pharmaceutical products. For example, polymorphs of the same drug may have substantial differences in such pharmaceutically important properties as dissolution rates and bioavailability. Likewise, different polymorphs may have different processing properties, such as hydroscopicity, flowability, and the like, which could affect their suitability as active pharmaceuticals for commercial production.

All TGA curves obtained from the present invention were carried out in a TGAQ500V620.6 Build 31 instrument with a ramp 10° C./minute up to 380° C. The infrared (IR) spectra, wherever provided, have been recorded on a Perkin Elmer System Spectrum 1 model spectrophotometer or Thermo Nexus 470 spectrometer, between 450 $cm^{-1}$ and 4000 $cm^{-1}$, with a resolution of 4 $cm^{-1}$ in a potassium bromide pellet, the test compound being at the concentration of 1% by weight. Differential scanning calorimetric analysis was carried out in a DSC Q200 V23 9 Build 78 model or DSC Q200 V23 10 Build 79 model from TA Instruments with a ramp of 10° C./minute to 300° C.

All XRPD data reported herein were obtained using a Bruker or PANalytical AXS D8 Advance Powder X-ray Diffractometer at Cu Kα radiation, having the wavelength 1.5418 Å. Since some margin of error is possible in the assignment of 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For all analytical data discussed in this application, it should be kept in mind that specific values depend on many factors, e.g., specific instrument, sample preparation and individual operator.

The present patent application provides amorphous form of pemetrexed disodium. In a broad aspect, any amorphous form of disodium salt of pemeterexed is contemplated, whether present in a substantially pure amorphous state or as part of a mixture. Particularly contemplated is a solid of disodium salt of pemetrexed that includes a large amorphous fraction, preferably more than 95% by weight, and a small crystalline fraction, preferably, more than 2% by weight. Non-solvated form of amorphous pemetrexed disodium, as well as solvated and hydrated forms are contemplated.

Figure 2:
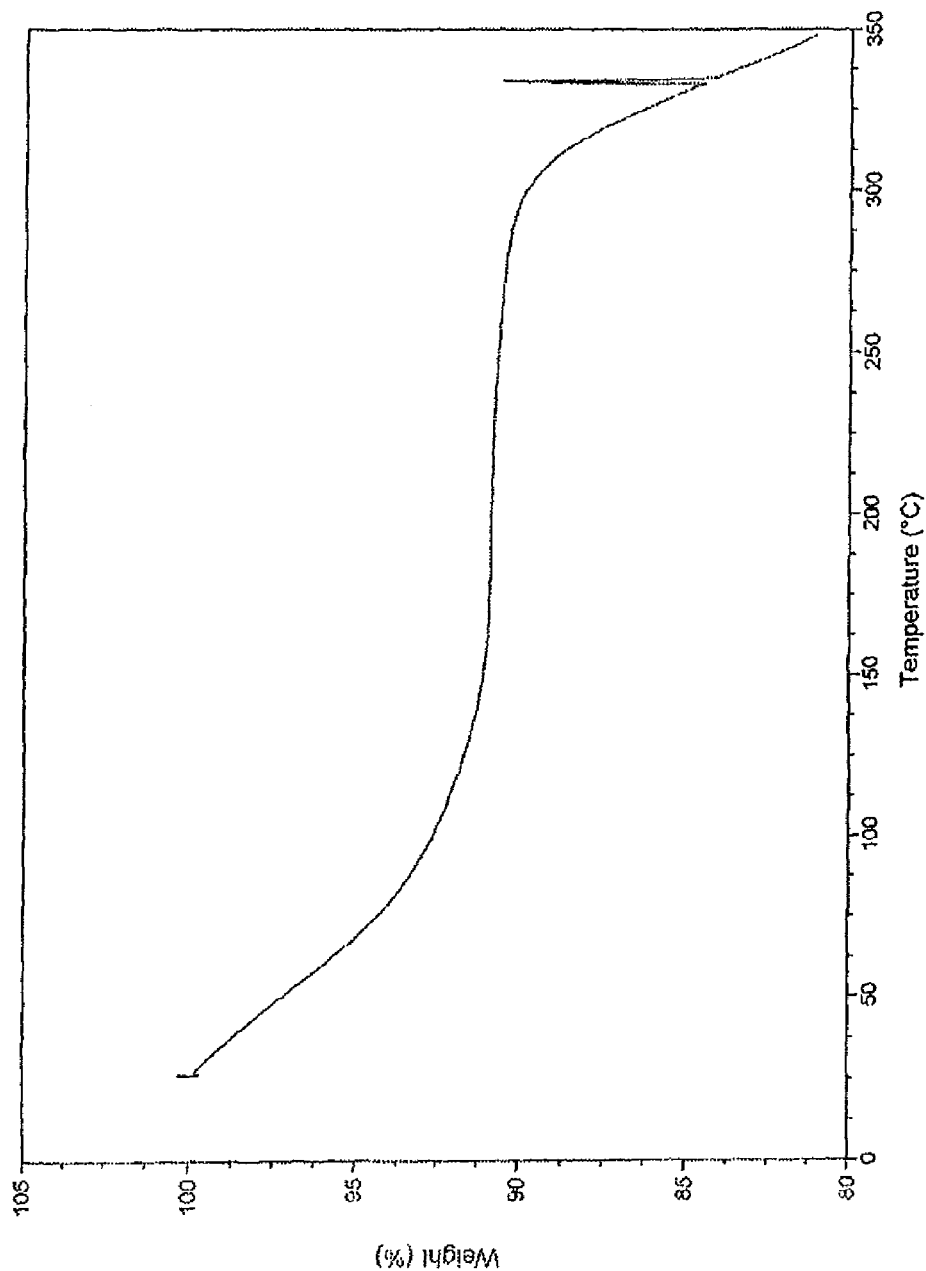
FIG. 2 shows an illustrative example of thermogravimetric analysis curve of amorphous pemetrexed disodium prepared according to Example 1.

FIG. 1 provides an example of XRPD pattern for amorphous solid of pemetrexed disodium. The amorphous pemetrexed disodium has a characteristic thermogravimetric curve (TGA) corresponding to a weight loss of about 8.268% w/w, as shown in FIG. 2. The process for making an amorphous form of pemetrexed is separately contemplated and set forth herein below in more detail.

In one embodiment, amorphous form of disodium salt of pemeterexed is present as component of a solid dispersion that includes i) disodium salt of pemetrexed in an amorphous form; and ii) a pharmaceutically-acceptable carrier. Preferably, the solid dispersion includes from about 10% to about 90% of disodium salt of pemetrexed; and from about 10% to about 90% of the carrier.

The solid dispersion may be prepared, for example, by dissolving a disodium salt of pemetrexed and the carrier in a solvent and removing the solvent. The preferred solvent are is water. The process of making the solid dispersion is separately contemplated and set forth below in more detail.

Figure 3:
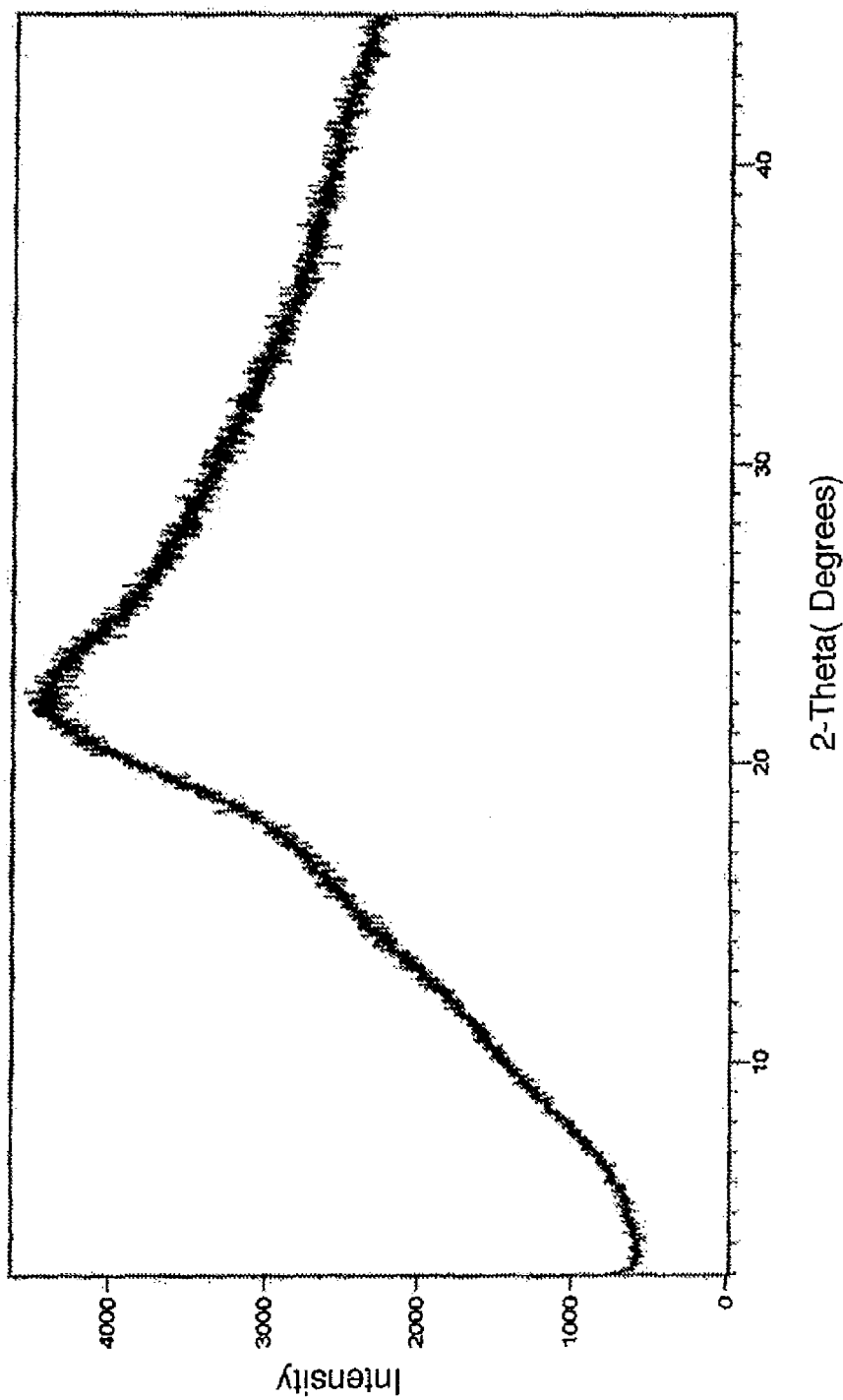
FIG. 3 shows an illustrative example of X-ray powder diffraction pattern of amorphous solid dispersion of pemetrexed disodium with Povidone K-30 prepared according to Example 5.
Figure 4:
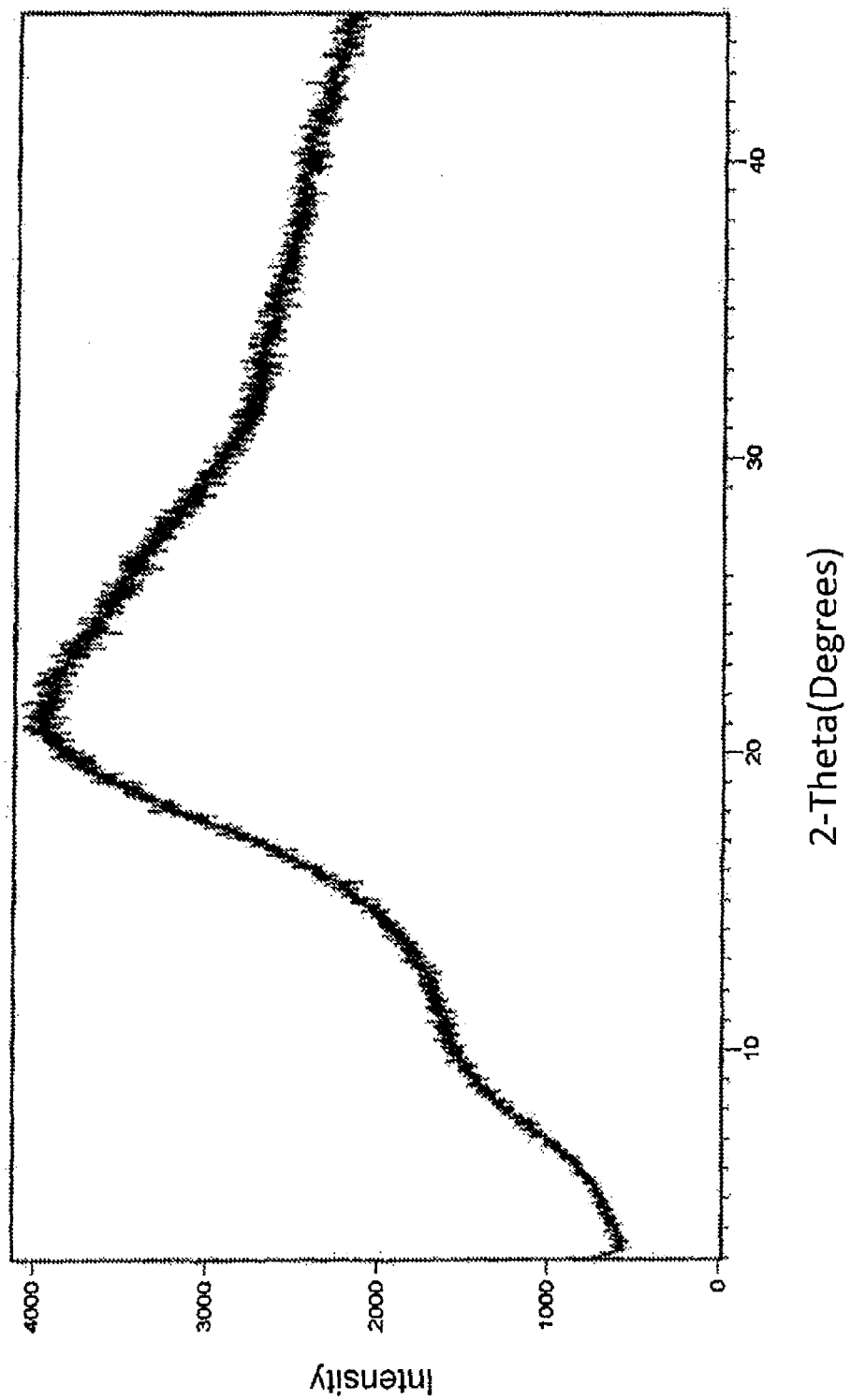
FIG. 4 shows an illustrative example of X-ray powder diffraction pattern of amorphous solid dispersion of pemetrexed disodium with HPMC prepared according to Example 6.
Figure 5:
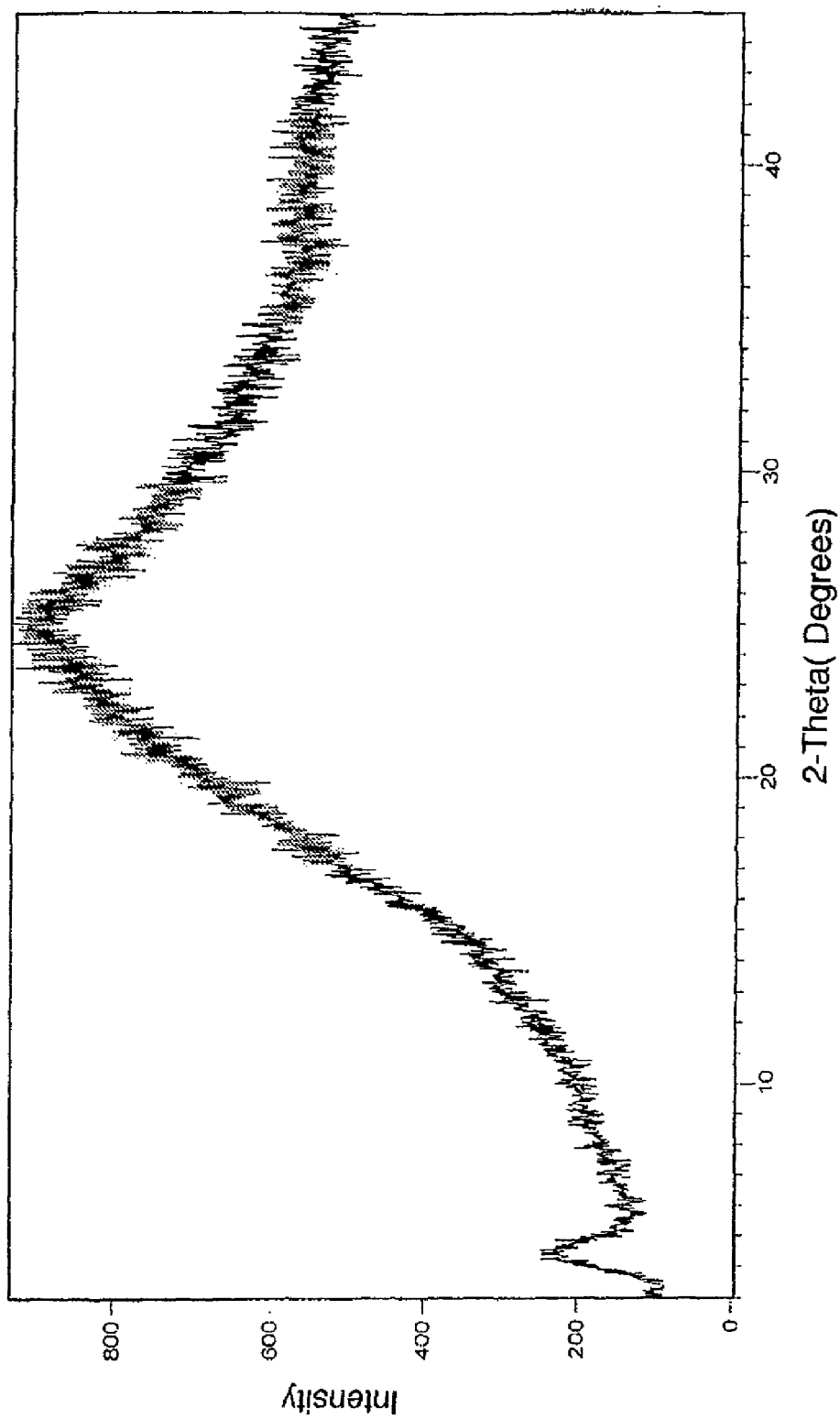
FIG. 5 shows an illustrative example of X-ray powder diffraction pattern of pemetrexed disodium prepared according to Example 7.
Figure 6:
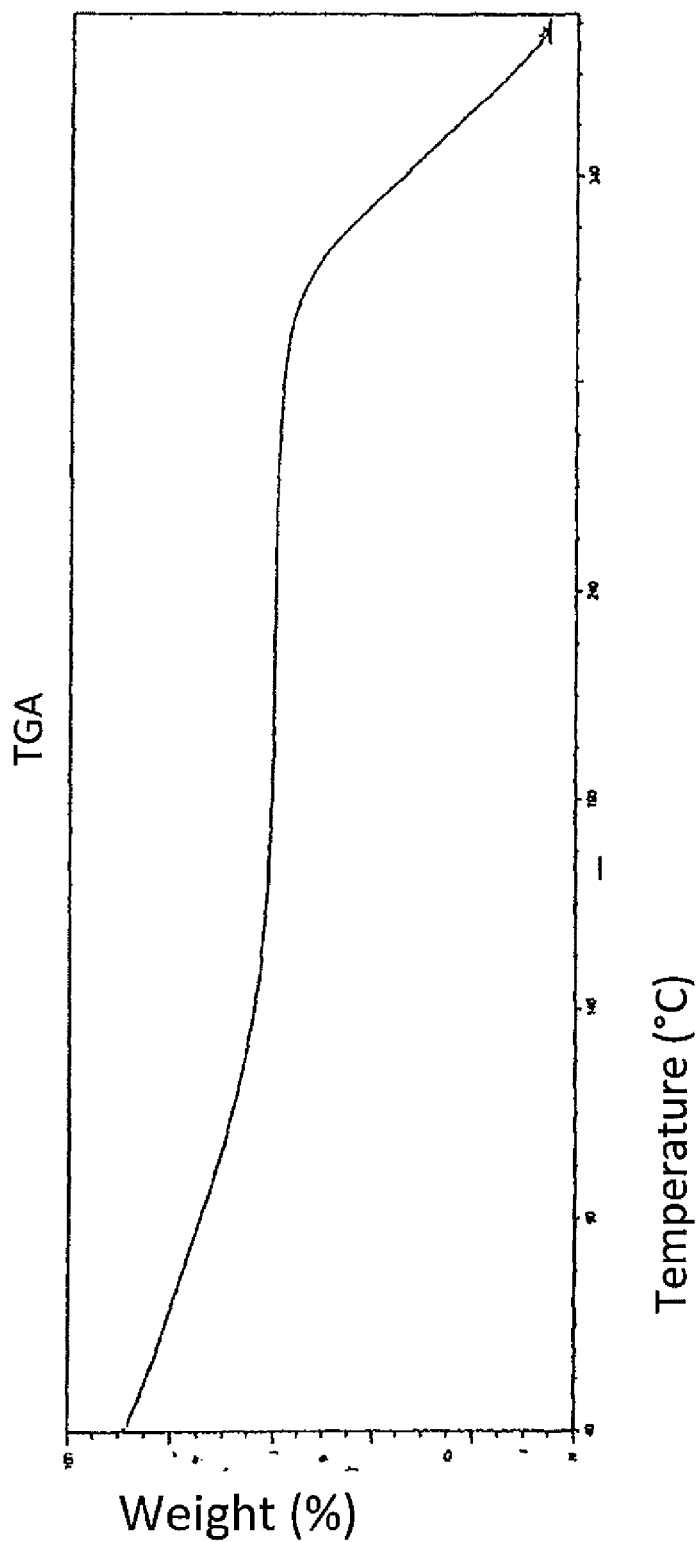
FIG. 6 shows an illustrative example of thermogravimetric analysis curve of pemetrexed disodium prepared according to Example 7.
Figure 7:
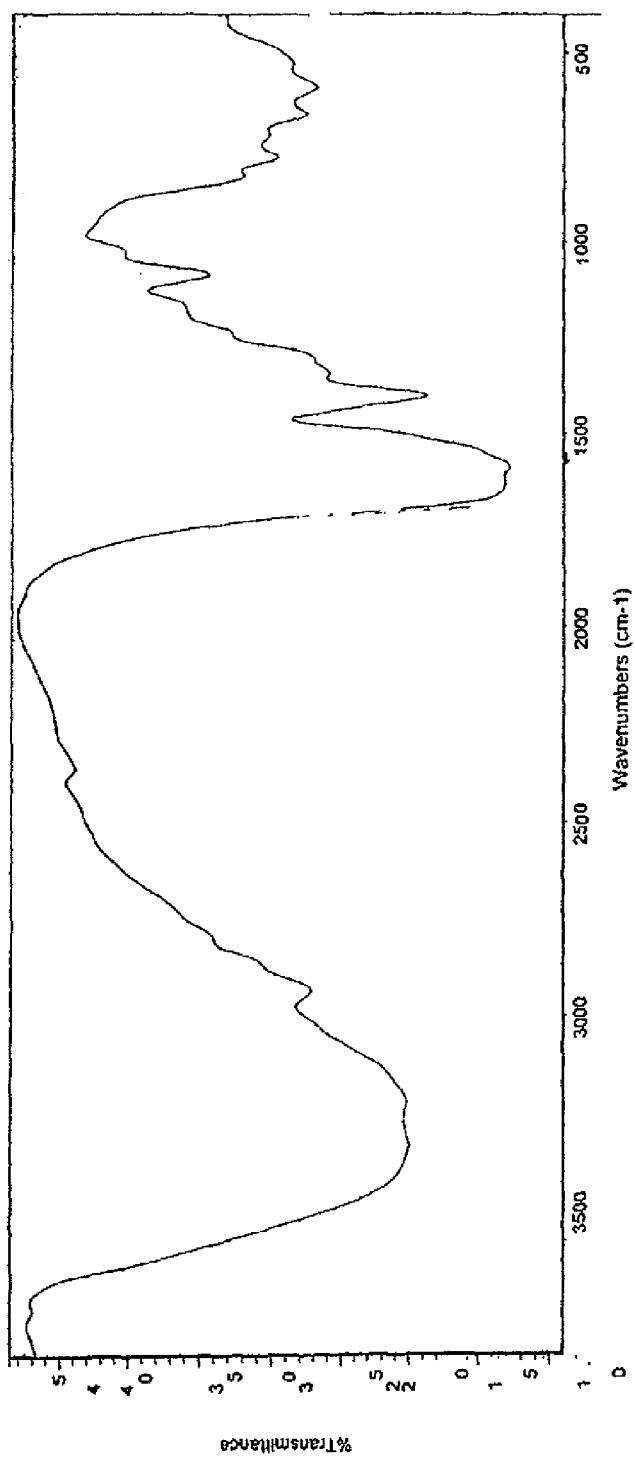
FIG. 7 shows an illustrative example of infrared absorption spectrum of pemetrexed disodium prepared according to Example 7.

The preferred carriers include cellulose derivatives and polyvinylpyrollidone. In one variant, the carrier is a cellulose derivative. The cellulose derivative is expected to have certain properties that make it useful as a carrier. Preferably, the cellulose derivative suitable as a carrier in the solid dispersion has sufficient solubility to dissolve in the liquid volatile solvent at levels sufficient to ensure the desired ratio of the components in the final dispersion and manufacturing suitability. Solubility in methanol may be used as a useful way to measure the desired solubility for the cellulose derivative of choice. It is preferred the suitable cellulose derivative possesses solubility in methanol equal to or greater than 0.01 g/ml, preferably, equal to or greater than 0.1 g/ml. In one variant, the cellulose derivative is hydroxypropylmethyl cellulose (HPMC). The XRPD of amorphous solid dispersion of pemetrexed disodium with Povidone-K-30 is illustrated in FIG. 3. The XRPD of amorphous solid dispersion of pemetrexed disodium with HPMC is illustrated in FIG. 4.

It is preferred that the solid dispersion has certain defined solubility characteristics to make it more suitable for use in pharmaceutical formulations. Preferably, the solid dispersion has solubility in water ranging from about 50 mg/ml to about 150 mg/ml. In one particular variant, which is separately contemplated, there is provided a solid dispersion that includes amorphous disodium salt of pemetrexed and HPMC in the ratio of 50:50 by weight which has solubility in water of about 83 mg/ml. In another particular variant, which is separately contemplated, there is provided a solid dispersion that includes amorphous disodium salt of pemetrexed and PVP in the ratio of 50:50 by weight which has solubility in water of about 137 mg/ml.

Separately contemplated is a process for making amorphous form of sodium salt of pemeterexed, in the form of a free solid or as a solid dispersion with at least one pharmaceutically acceptable carrier, which process includes:

i) providing a solution of pemetrexed disodium, alone or in combination with pharmaceutically acceptable carrier, in a solvent; and ii) removing the solvent.

Step i) involves providing a solution of pemetrexed disodium. Providing a solution of pemetrexed disodium includes dissolving pemetrexed disodium either alone or optionally in combination with pharmaceutically acceptable carrier in a solvent or a mixture of solvents, or such a solution may be obtained directly from a reaction in which pemetrexed disodium is formed. Any polymorphic form may be used in the preparation of solution such as crystalline or semicrystalline forms, including solvates and hydrates.

The solvent may be water, dimethylsulfoxide (DMSO); dimethylformamide (DMF); alcohols such as isopropyl alcohol (IPA) and methanol; ketones such as acetone, ethyl methyl ketone, and methyl isobutyl ketone; and mixtures thereof. The preferred solvents are water or aqueous alcoholic solutions. The dissolution temperature may range from about 20° C. to about 100° C. or reflux temperature of the solvent. Preferably, dissolution is carried out at a room temperature.

The quantity of solvent used for dissolution depends on the solvent and the dissolution temperature opted for the process.

The concentration of pemetrexed disodium in the solution may generally range from about 0.1 to about 10 g/ml in the solvent.

When the solution of pemetrexed disodium is prepared along with a pharmaceutically acceptable carrier, the order of charging the different materials is not critical for the product obtained. A specific order may be preferred with respect to the equipment actually used and will be easily determined by a person skilled in the art. In any case, the pemetrexed disodium must be completely soluble in the solvent and should provide a clear solution. The presence of undissolved crystals could lead to the formation of a material, which is not completely amorphous. Pemetrexed disodium and the pharmaceutically acceptable carrier used can be dissolved either in the same solvent or they may be dissolved in different solvents and then combined to form a mixture.

If desired, the solution may be filtered to remove the undissolved particles. The undissolved particles may be removed suitably by filtration, centrifugation, decantation, and other techniques. The solution may be filtered by passing through paper, glass fiber, or other membrane material, or a clarifying agent such as celite. Depending upon the equipment used and the concentration and temperature of the solution, the filtration apparatus may need to be preheated to avoid premature crystallization.

Pharmaceutically acceptable carriers that may be used for the preparation of amorphous solid dispersion of pemetrexed disodium include, but are not limited to, pharmaceutical hydrophilic carriers such as polyvinylpyrrolidone (homopolymers or copolymers of N-vinylpyrrolidone; povidone), gums, cellulose derivatives (including hydroxypropyl methylcellulose (HPMC), hydroxypropyl cellulose, manitol and others), cyclodextrins, gelatins, hypromellose phthalate, sugars, polyhydric alcohols, polyethylene glycol, polyethylene oxides, polyoxyethylene derivatives, polyvinyl alcohol, propylene glycol derivatives and the like. The use of mixtures of more than one of the pharmaceutical carriers to provide desired release profiles or for the enhancement of stability is within the scope of this invention. Also, all viscosity grades, molecular weights, commercially available products, their copolymers, mixtures are all within the scope of this invention without limitation.

These lists of solvents and pharmaceutically acceptable carriers are merely representative of those that can be used, and the lists are not intended to be exhaustive.

Step ii) involves removing the solvent. Removal of the solvent may be carried out suitably using techniques such as evaporation, atmospheric distillation, or distillation under vacuum. Suitable techniques which may be used for solvent removal include spray drying, distillation using a rotational evaporator device such as a Buchi Rotavapor, agitated thin film drying ("ATFD"), and the like. These techniques are applicable to both aqueous and organic solutions of pemetrexed disodium and mixtures of pemetrexed disodium with a pharmaceutically acceptable carrier. However, solutions using the more volatile organic solvents generally provide easier processing.

Preferably, removal of the solvent is done by spray drying of a solution of pemetrexed disodium or its mixture with the pharmaceutically acceptable carrier.

The amorphous pemetrexed disodium or amorphous solid dispersion of pemetrexed disodium with pharmaceutically acceptable carrier obtained by spray drying process may be suitably utilized for the preparation of pharmaceutical compositions.

Spray drying and ATFD are more suitable for industrial scale production with a batch size of about 100 g or about 1 kg, or greater. Other techniques such as Buchi Rota-vapor drying and dry distillation under vacuum may be suitable for laboratory-scale processes such as for quantities less than about 100 g.

Evaporation of the solvent may be conducted under a vacuum, such as below about 100 mm Hg to below about 600 mm Hg, at temperatures such as about −30° C. to about 100° C. Any temperature and vacuum conditions can be used as long as there is no increase in the impurity levels and any major variations in the product characteristics.

The amorphous material obtained from step ii) may be collected from the equipment using techniques such as by scraping, or by shaking the container, or using techniques specific to the particular apparatus.

The product may be dried, if desired.

Drying may be carried out under reduced pressure until the residual solvent content reduces to an amount that is within the limits given by the International Conference on Harmonisation of Technical Requirements for Registration of Pharmaceuticals for Human Use ("ICH") guidelines. The guideline solvent level depends on the type of solvent but is not more than about 5000 ppm, or preferably about 4000 ppm, or more preferably about 3000 ppm.

The drying can be carried out at reduced pressures, such as below about 650 mmHg or below about 50 mmHg, at temperatures such as about 35° C. to about 70° C. The drying can be carried out for any desired time period that achieves the desired result, such as times about 1 to 20 hours, or longer. Drying may also be carried out for shorter or longer periods of time depending on the product specifications.

Drying can be suitably carried out in equipment such as a tray dryer, vacuum oven, air oven, or using a fluidized bed drier, spin flash dryer, and flash dryer.

It is generally preferred that a rapid drying is often utilized to provide the desired amorphous form free from residual organic solvent.

The amorphous material obtained as pemetrexed disodium or its hydrate or its solid dispersion may have water content of about 15% w/w or less. In some extended exposure conditions, it may acquire moisture up to about 21%, however, the amorphous form remain retained significantly. In a preferred embodiment, the water content may range of about 5% to about 10% w/w.

Separately contemplated is a composition containing solid disodium salt of pemetrexed, of which at least 50%, by total weight of the solid disodium salt of pemetrexed in the composition, is in the amorphous form. In the more preferred form of this composition, the solid disodium salt of pemetrexed is suitable for use as active ingredient in formulating pharmaceutical products. The remainder of the solid disodium salt of pemetrexed in the composition, i.e., 50% or less of the total weight of disodium salt of pemetrexed, may be crystalline forms. An example of crystalline form is the crystalline form of disodium salt of pemetrexed described herein below. Other examples of crystalline forms of disodium salt of pemetrexed are described, for example, in US 2008/0045711, which is incorporated herein by reference for the purpose stated and in its entirety. In an embodiment, the composition may include at least 90% of the amorphous form of disodium salt of pemetrexed with respect to total weight of the solid disodium salt of pemetrexed in the composition. In another embodiment, the composition may include at least 95% of the amorphous form of disodium salt of pemetrexed with respect to the total weight of the solid disodium salt of pemetrexed in the composition. In a particular variant of this embodiment, the composition includes more than 2% of a crystalline form of disodium salt of pemetrexed. In yet another embodiment, the composition is substantially free of any forms of disodium salt of pemetrexed other than its amorphous form.

The composition containing a mixture of amorphous and crystalline forms may be prepared for example by direct mixing of amorphous and crystalline portions. Also, with respect to specific variant described below, the composition may be prepared as described below.

X-ray diffraction provides a convenient and practical means for quantitative determination of the relative amounts of crystalline and/or amorphous forms in a solid mixture. X-ray diffraction is adaptable to quantitative applications because the intensities of the diffraction peaks of a given compound in a mixture are proportional to the fraction of the corresponding powder in the mixture. The percent composition of crystalline disodium salt of pemetrexed in an unknown composition can be determined. Preferably, the measurements are made on solid powder disodium salt of pemetrexed. The X-ray powder diffraction patterns of an unknown composition may be compared to known quantitative standards containing pure crystalline forms of disodium salt of pemetrexed to identify the percent ratio of a particular crystalline form. If amorphous form is the major fraction of the composition, the amount may be further compared to the total weight of the solid subject to analysis. This is done by comparing the relative intensities of the peaks from the diffraction pattern of the unknown solid powder composition with a calibration curve derived from the X-ray diffraction patterns of pure known samples. The curve can be calibrated based on the X-ray powder diffraction pattern for the strongest peak from a pure sample of crystalline forms of disodium salt of pemetrexed. The calibration curve may be created in a manner known to those of skill in the art. For example, five or more artificial mixtures of crystalline forms of disodium salt of pemetrexed, at different amounts, may be prepared. In a non-limiting example, such mixtures may contain, 2%, 5%, 7%, 8%, and 10% of disodium salt of pemetrexed for each crystalline form. Then, X-ray diffraction patterns are obtained for each artificial mixture using standard X-ray diffraction techniques. Slight variations in peak positions, if any, may be accounted for by adjusting the location of the peak to be measured. The intensities of the selected characteristic peak(s) for each of the artificial mixtures are then plotted against the known weight percentages of the crystalline form. The resulting plot is a calibration curve that allows determination of the amount of the crystalline forms of disodium salt of pemetrexed in an unknown sample. For the unknown mixture of crystalline and amorphous forms of disodium salt of pemetrexed, the intensities of the selected characteristic peak(s) in the mixture, relative to an intensity of this peak in a calibration mixture, may be used to determine the percentage of the given crystalline form in the composition, with the remainder determined to be the amorphous material. The overall crystallinity may be determined as follows:

% Crystallinity=$(C/A+C-B) \times 100$, where C is area under crystalline peaks, A is area under amorphous halo, and B is background noise due to air scattering, fluorescence, etc.

In a particular variant, the present patent application provides a composition containing a major amount of amorphous form of disodium salt of pemetrexed and minor amount of crystalline form of disodium salt of pemetrexed. Preferably, the composition contains more than 50% of amorphous form of disodium salt of pemetrexed and at least 5% of crystalline form of disodium salt of pemetrexed. For this variant, it is particularly contemplated that the crystalline form of disodium salt of pemetrexed is the polymorph with X-ray powder diffraction pattern having peaks as set forth in Table 1:

TABLE 1

| Degree 2-Theta | d-spacing [Å] | Intensity [%] |
| --- | --- | --- |
| 4.0 | 21.9 | 25.9 |
| 4.4 | 19.8 | 18.5 |
| 7.8 | 11.2 | 4.3 |
| 9.3 | 9.4 | 6.6 |
| 12.6 | 6.9 | 3.2 |
| 17.2 | 5.1 | 21.7 |
| 18.0 | 4.9 | 100 |
| 19.4 | 4.5 | 21.0 |
| 20.3 | 4.3 | 33.5 |
| 21.0 | 4.2 | 66.1 |
| 24.2 | 3.6 | 2.3 |
| 25.9 | 3.4 | 17.2 |
| 27.5 | 3.2 | 14.2 |
| 29.0 | 3.0 | 16.0 |
| 36.2 | 2.4 | 4.7 |
| 43.2 | 2.0 | 41.4 |

Figure 8:
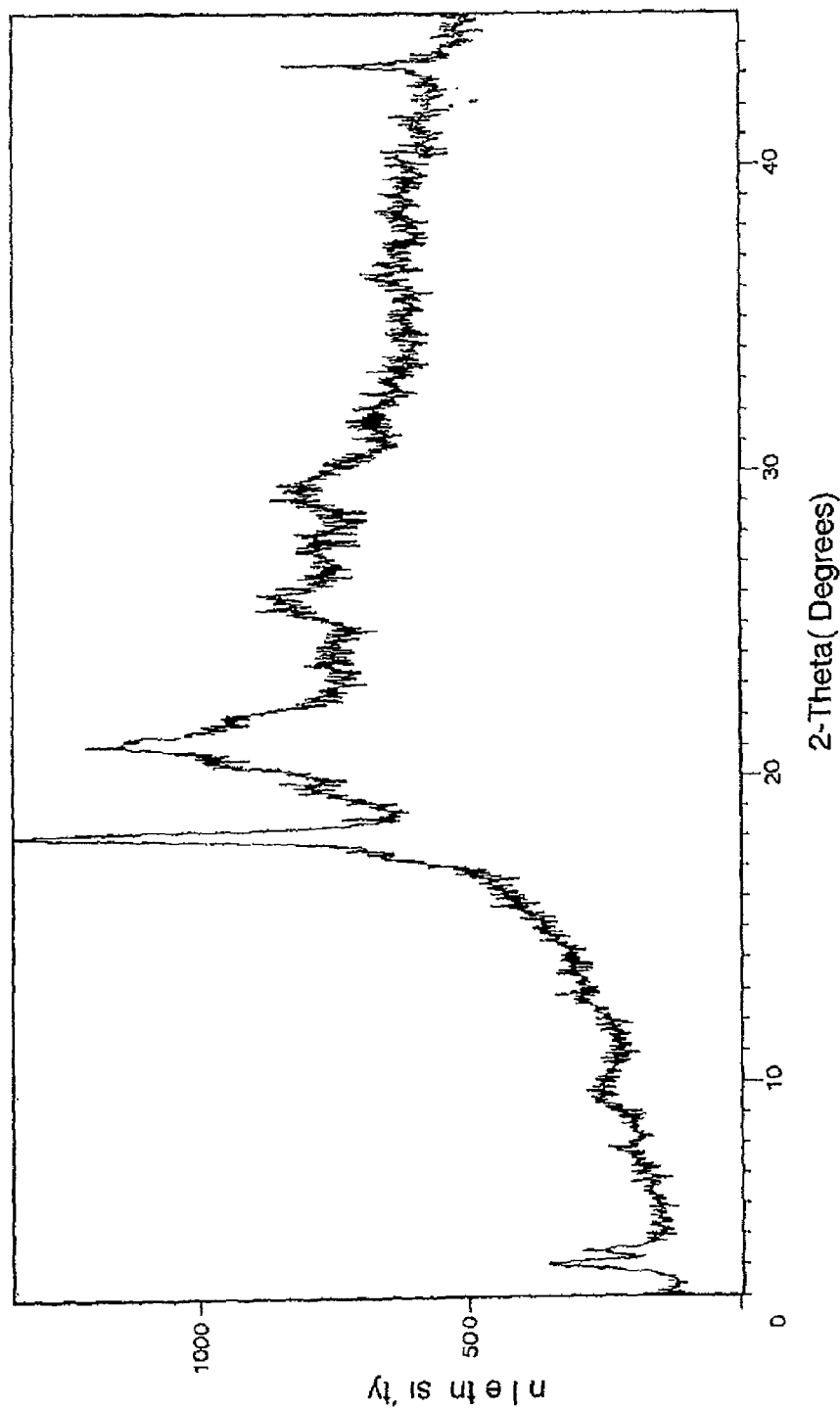
FIG. 8 shows an illustrative example of X-ray powder diffraction pattern of solid disodium salt of pemetrexed prepared according to Example 8.

FIG. 8 shows an example of the XRD for the composition as described above. A composition containing a mixture of amorphous and crystalline forms of disodium salt of pemetrexed substantially in accordance with FIG. 8 is separately contemplated.

While the invention is not limited to any specific theory, it is believed that the crystalline form of disodium Form III has characteristic peaks at diffraction angles (2 theta) at 4.0, 17.3, 18.0, 19.5, 20.4, 21.0, 29.0 and 43.3, ±0.2 degrees. Each peak is shown with measurement permissible error of ±0.2 degrees. This crystalline form of disodium salt of pemetrexed, hereby designated as Form III, is separately contemplated. The process for making the mixture of amorphous and crystalline forms of pemetrexed, in particular for making the specific variant described herein is described in greater detail below.

Also provided is a process for making the composition, which is a mixture of amorphous and crystalline forms of disodium salt of pemetrexed, the process including:

i) providing a solution of disodium salt of pemetrexed in water;

ii) adding an organic hydrocarbon solvent which is capable of forming an azeotropic mixture with water; and iii) carrying out an azeotropic distillation until a solid is obtained.

The first step involves providing a solution of pemetrexed disodium in water. This may be accomplished by dissolving pemetrexed disodium in water or a mixture of water with the solvent, or such a solution may be obtained directly from a reaction in which pemetrexed disodium is formed. Any polymorphic form may be used in the preparation of solution such as crystalline or semi-crystalline forms, including solvates and hydrates. The dissolution temperature may range from about 20° C. to about 100° C. or reflux temperature of the solvent. Preferably dissolution is carried out at a room temperature.

The quantity of solvent used for dissolution depends on the solvent and the dissolution temperature opted for the process. The concentration of pemetrexed disodium in the solution may generally range from about 0.1 to about 10 g/ml in the solvent.

The water may be then removed by azeotropic distillation with the organic hydrocarbon solvent. Suitable organic hydrocarbon solvent for the preparation of the composition containing the mixture of solid forms may be selected from toluene, xylenes or the like, preferably toluene.

Suitable temperature for the preparation of Form III depends on the ratio of water and organic hydrocarbon solvent of the pemetrexed disodium solution. For instance, when the solvent is a mixture of water and toluene in 12.2:87.8 v/v ratio, the temperature is about 100-105° C.

If desired, the solid may be dried to afford the desired solid. Drying can be carried out under reduced pressure until the residual solvent content reduces to an amount that is within the limits given by the International Conference on Harmonisation of Technical Requirements for Registration of Pharmaceuticals for Human Use ("ICH") guidelines. The guideline solvent level depends on the type of solvent but is not more than about 5000 ppm, or preferably about 4000 ppm, or more preferably about 3000 ppm.

The drying can be carried out at reduced pressures, such as below about 650 mmHg or below about 50 mmHg, at temperatures such as about 35° C. to about 70° C. The drying can be carried out for any desired time period that achieves the desired result, such as times about 1 to 20 hours, or longer. Drying may also be carried out for shorter or longer periods of time depending on the product specifications.

Drying can be carried out in equipment such as a tray dryer, vacuum oven, air oven, or using a fluidized bed drier, spin flash dryer, and flash dryer.

It is generally preferred that a rapid drying is often utilized to provide the desired crystalline form free from residual organic solvent.

The solid pemetrexed disodium that includes crystalline Form III obtained as described herein may have amorphous content more than about 50 wt %. In one variant, the pemetrexed disodium that includes crystalline Form III may include about 50 wt % to about 60 wt % of amorphous material.

Figure 9:
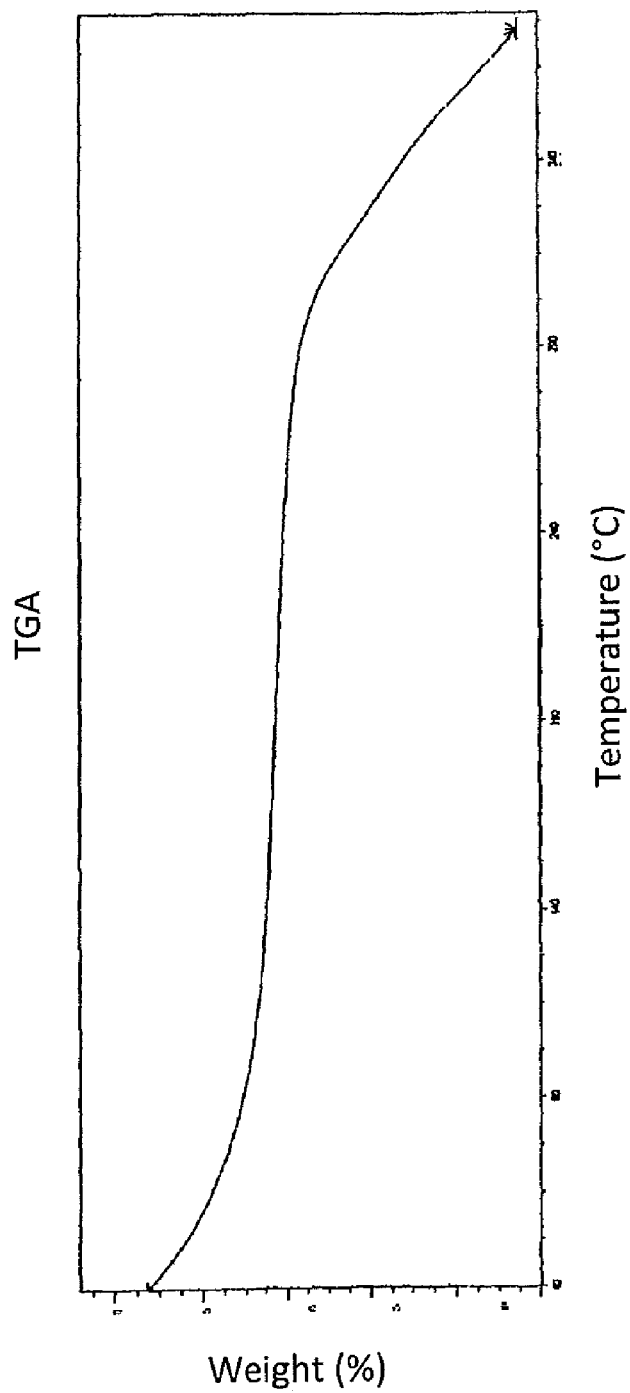
FIG. 9 shows an illustrative example of thermogravimetric analysis curve of solid disodium salt of pemetrexed prepared according to Example 8.
Figure 10:
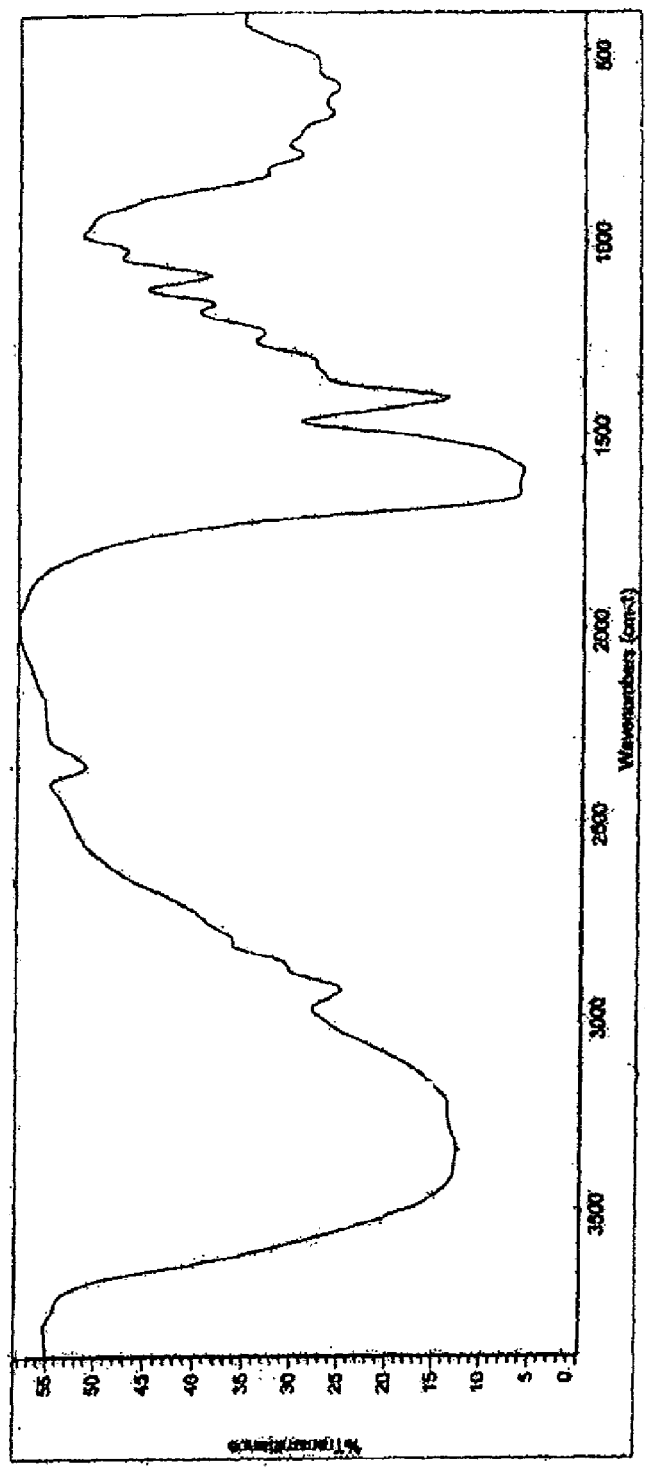
FIG. 10 shows an illustrative example of infrared absorption spectrum solid disodium salt of pemetrexed prepared according to Example 8.
Figure 11:
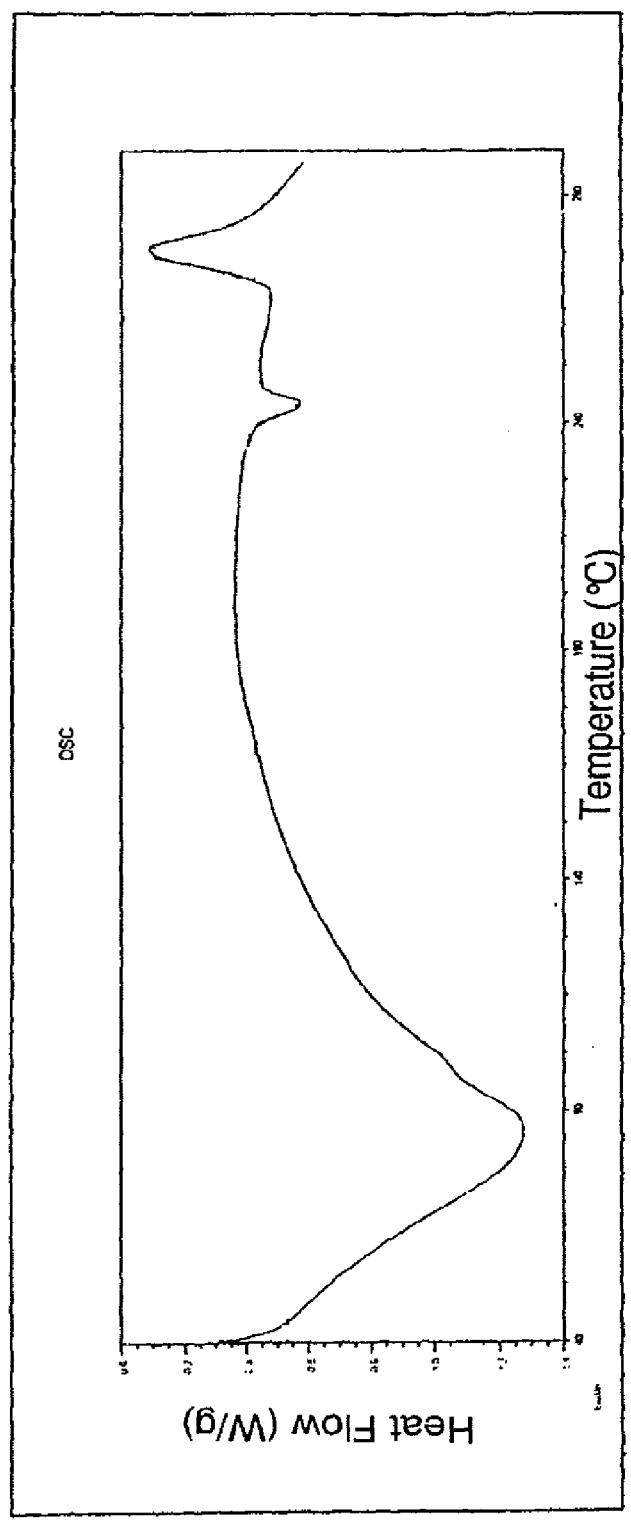
FIG. 11 shows an illustrative example of differential scanning calorimetry thermogram of solid disodium salt of pemetrexed prepared according to Example 8.

Pemetrexed disodium containing a mixture of amorphous solid and crystalline Form III has a characteristic thermogravimetric curve (TGA) corresponding to a weight loss of about 22% w/w, as shown in FIG. 9. Pemetrexed disodium containing a mixture of amorphous solid and crystalline Form III has an infrared absorption spectrum in potassium bromide comprising peaks at about 3340, 2930, 2355, 1596, 1403, 1089, and 596, ±5 cm$^{-1}$. Infrared absorption spectrum of Pemetrexed disodium containing a mixture of amorphous solid and crystalline Form III recorded with potassium bromide is substantially in accordance with the spectrum of FIG. 10. Pemetrexed disodium containing a mixture of amorphous solid and crystalline Form III is further characterized by its DSC thermogram, which is substantially in accordance with FIG. 11. Pemetrexed disodium semi-crystalline Form III is further characterized by its DSC curve having endothermic peaks at about 86, 244, and 271° C., and an exothermic peak at about 278° C.

Figure 12:
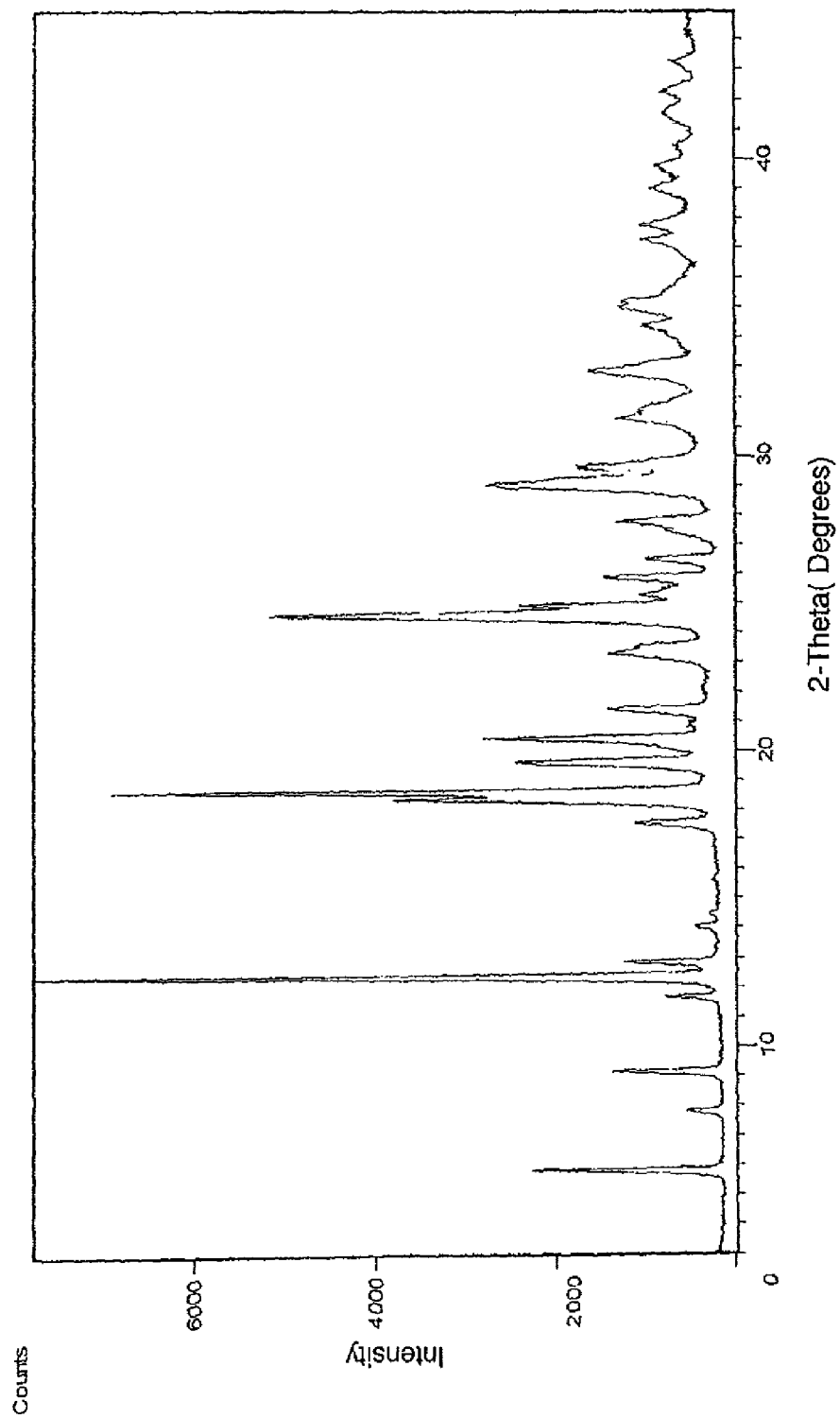
FIG. 12 shows an illustrative example of X-ray powder diffraction pattern of crystalline Form A of pemetrexed prepared according to Example 9.
Figure 13:
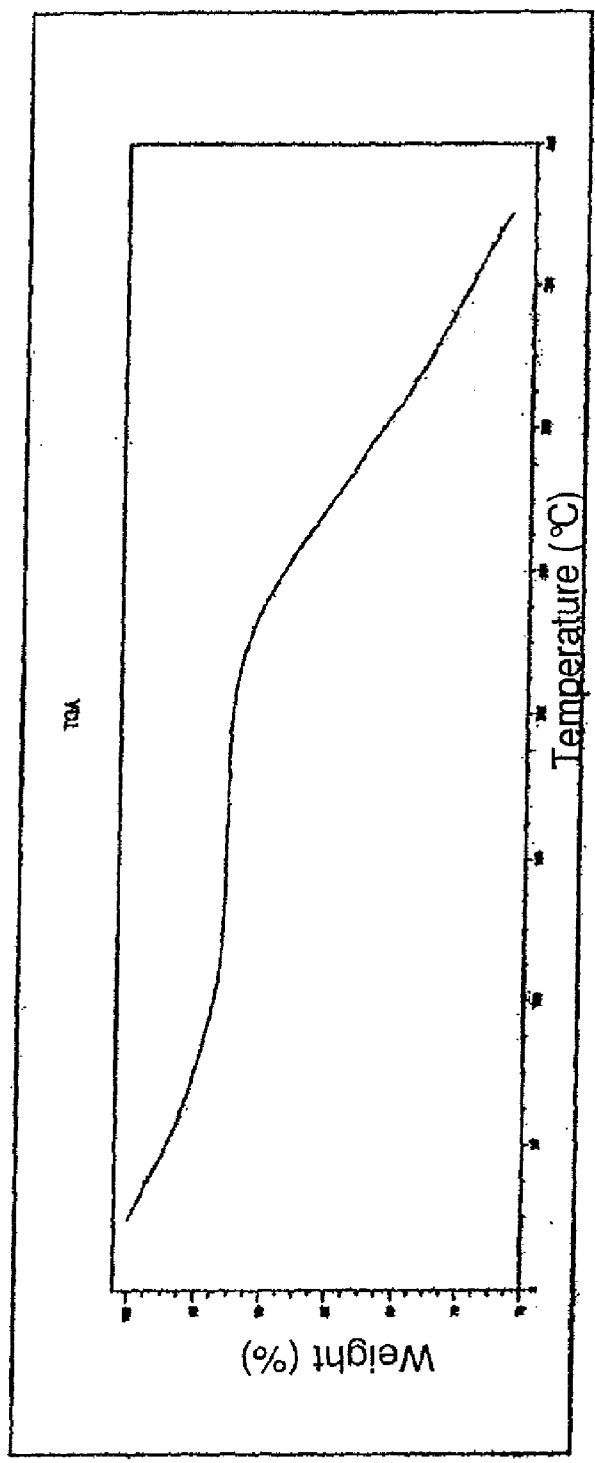
FIG. 13 shows an illustrative example of thermogravimetric analysis curve of crystalline Form A of pemetrexed prepared according to Example 9.
Figure 14:
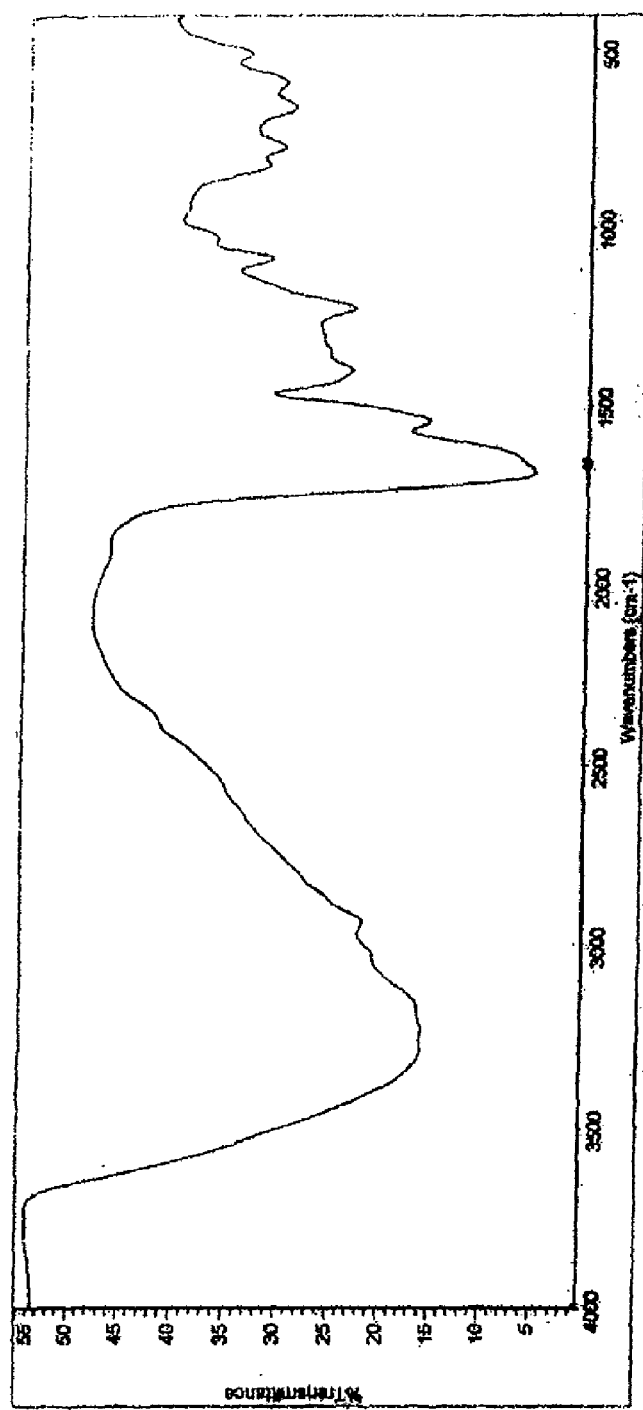
FIG. 14 shows an illustrative example of infrared absorption spectrum of crystalline Form A of pemetrexed prepared according to Example 9.

Also provided is crystalline Form A of pemetrexed diacid, which has XRPD pattern with characteristic peaks at approximately: 5.8, 12.4, 18.3, 18.6, 19.6, 20.4, 24.5, 24.9, 25.8, 28.9, 29.2, 29.6, and 32.8, ±0.2 degrees 2θ. The pemetrexed diacid having XRPD pattern substantially in accordance with FIG. 12 in separately contemplated. Pemetrexed diacid crystalline Form A has a characteristic thermogravimetric (TGA) curve corresponding to a weight loss of about 26% w/w, as shown in FIG. 13. Pemetrexed diacid crystalline Form A is characterized by an infrared absorption spectrum in potassium bromide comprising peaks at about 3286, 3228, 2940, 1685, 1543.9, 1399, 1348, 1300, 1226, and 663, ±5 cm$^{-1}$. Pemetrexed diacid crystalline Form A having infrared absorption spectrum in potassium bromide substantially in accordance with the spectrum of FIG. 14 is separately contemplated.

Figure 15:
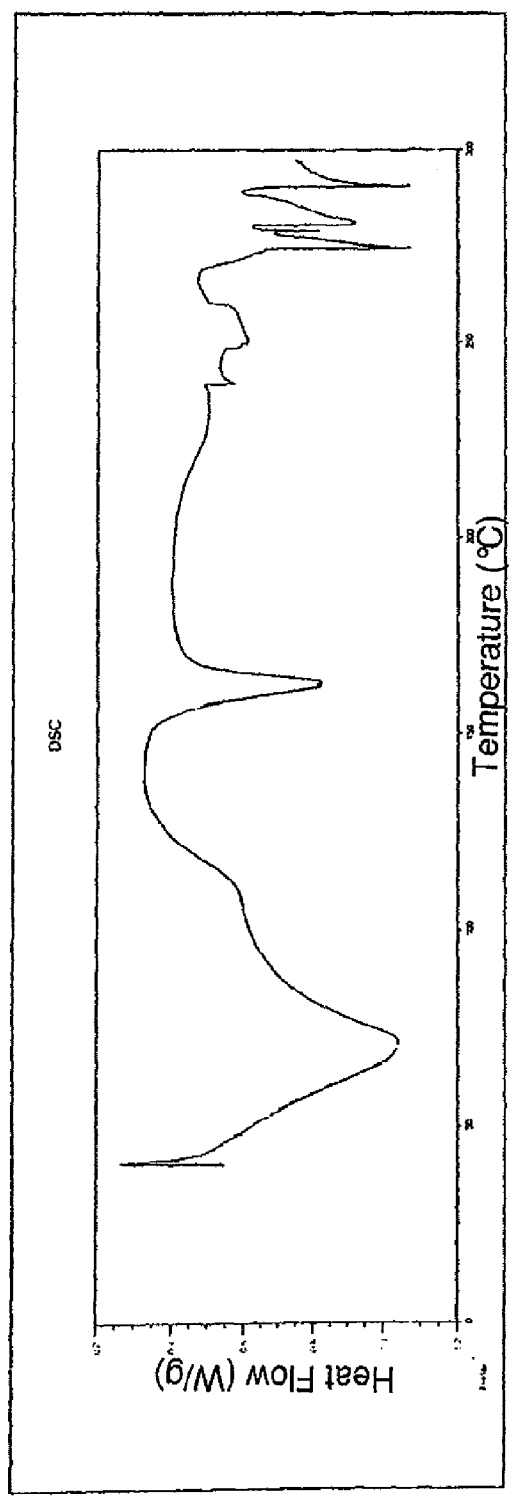
FIG. 15 shows an illustrative example of differential scanning calorimetry curve of crystalline Form A of pemetrexed prepared according to Example 9.

Pemetrexed diacid crystalline Form A is further characterized by its DSC thermogram, which is shown in FIG. 15, having endothermic peaks at about 71, and 163° C.

The process for the preparation of pemetrexed diacid crystalline Form A includes reacting Dimethyl N-[4-(2-{4-hydroxy-6-aminopyrrolo-[2,3-d]pyrimidin-3-yl}ethyl)benzoyl]-L-glutamic acid PTSA salt with aqueous sodium hydroxide solution, followed by neutralization with an acid up to a pH about 3 in the presence of ethanol. Acid utilized for neutralization may be selected from hydrochloric acid, hydrobromic acid, sulfuric acid, acetic acid, p-toluene sulfuric acid, and the like. Suitable temperature for conducting the reaction may range from about 20° C. to about 80° C.

Figure 16:
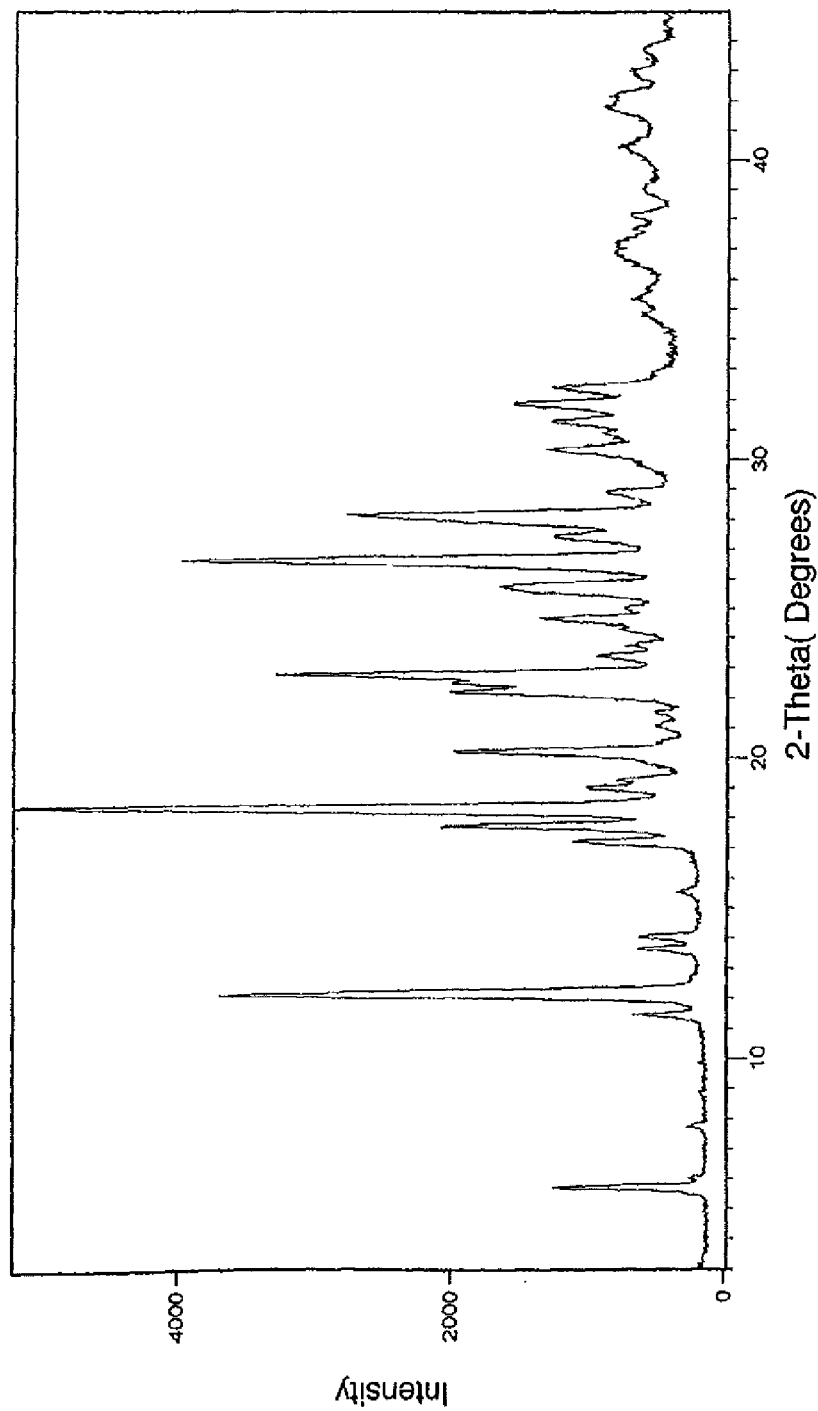
FIG. 16 shows an illustrative example of X-ray powder diffraction pattern of crystalline Form B of pemetrexed prepared according to Example 10.
Figure 17:
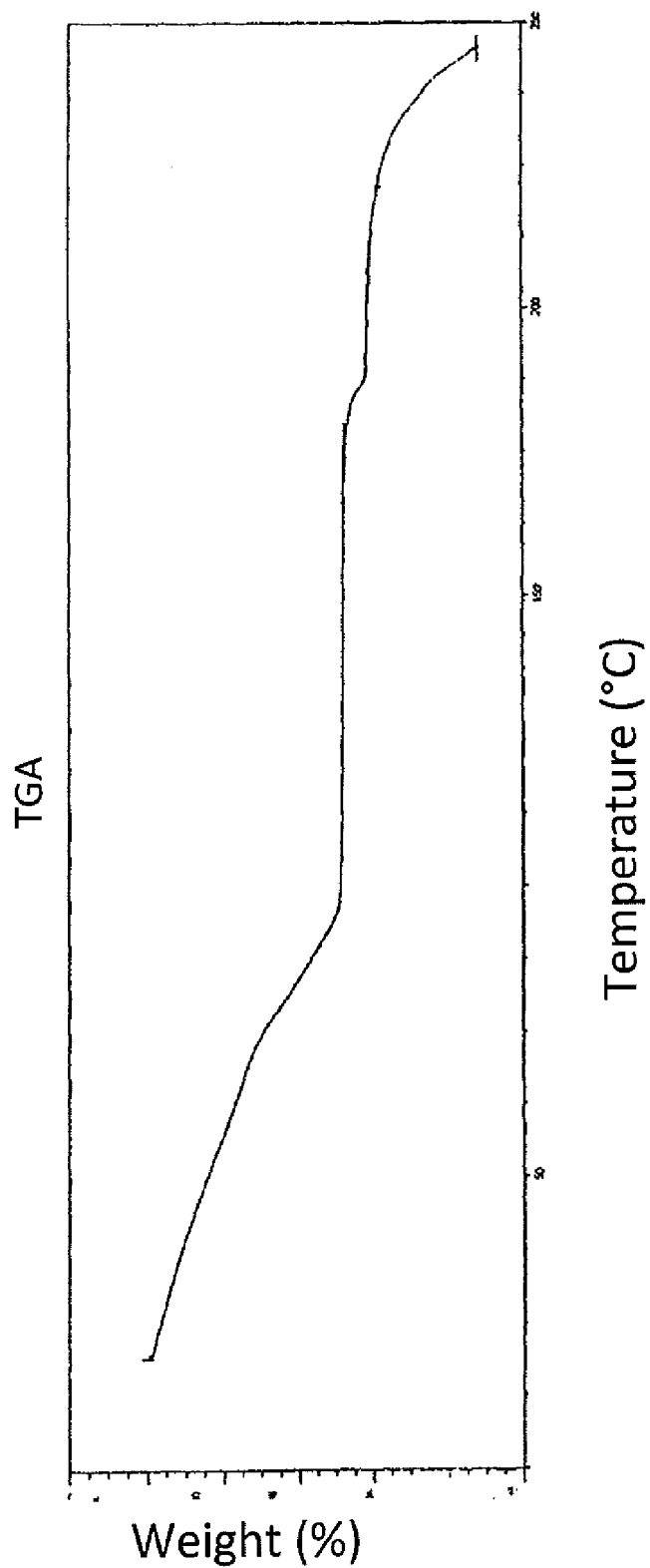
FIG. 17 shows an illustrative example of thermogravimetric analysis curve of crystalline Form B of pemetrexed prepared according to Example 10.
Figure 18:
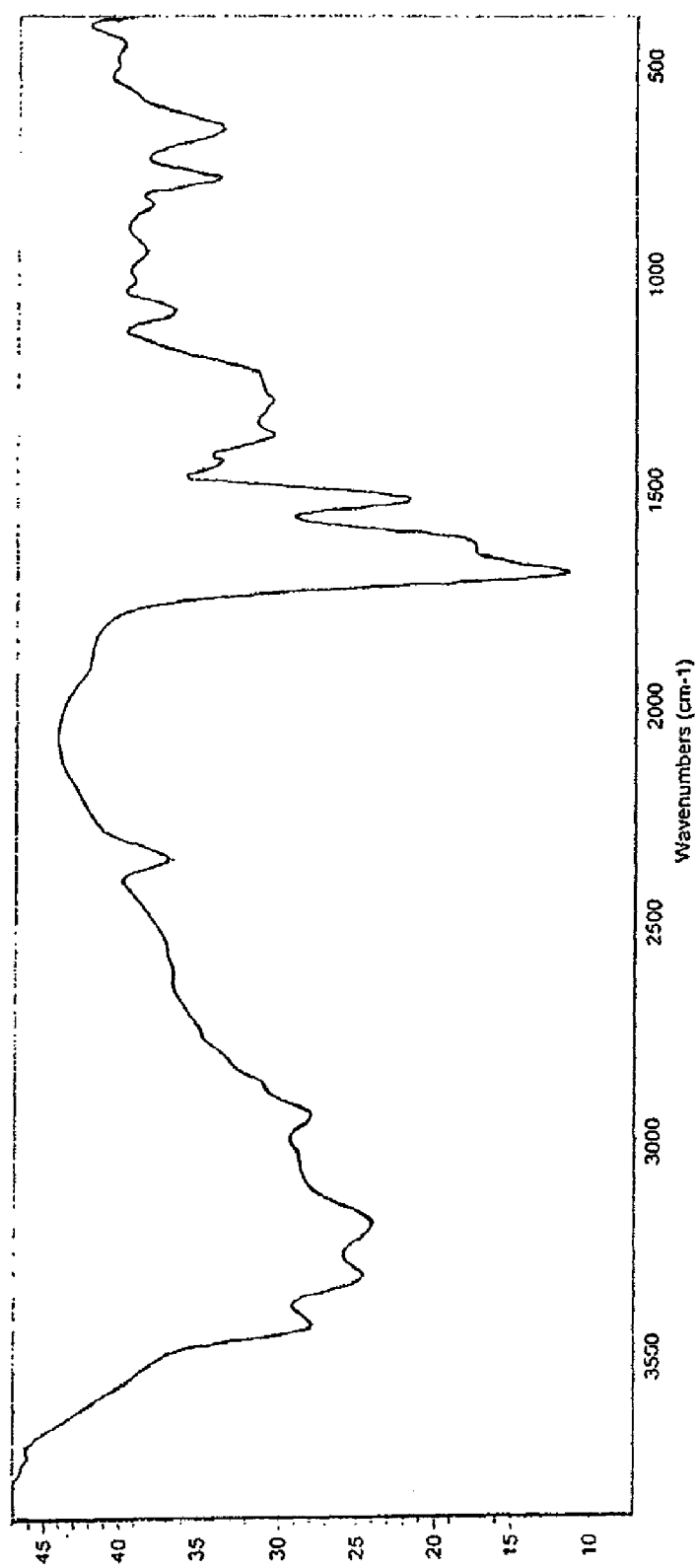
FIG. 18 shows an illustrative example of infrared absorption spectrum of crystalline Form B of pemetrexed prepared according to Example 10.
Figure 19:
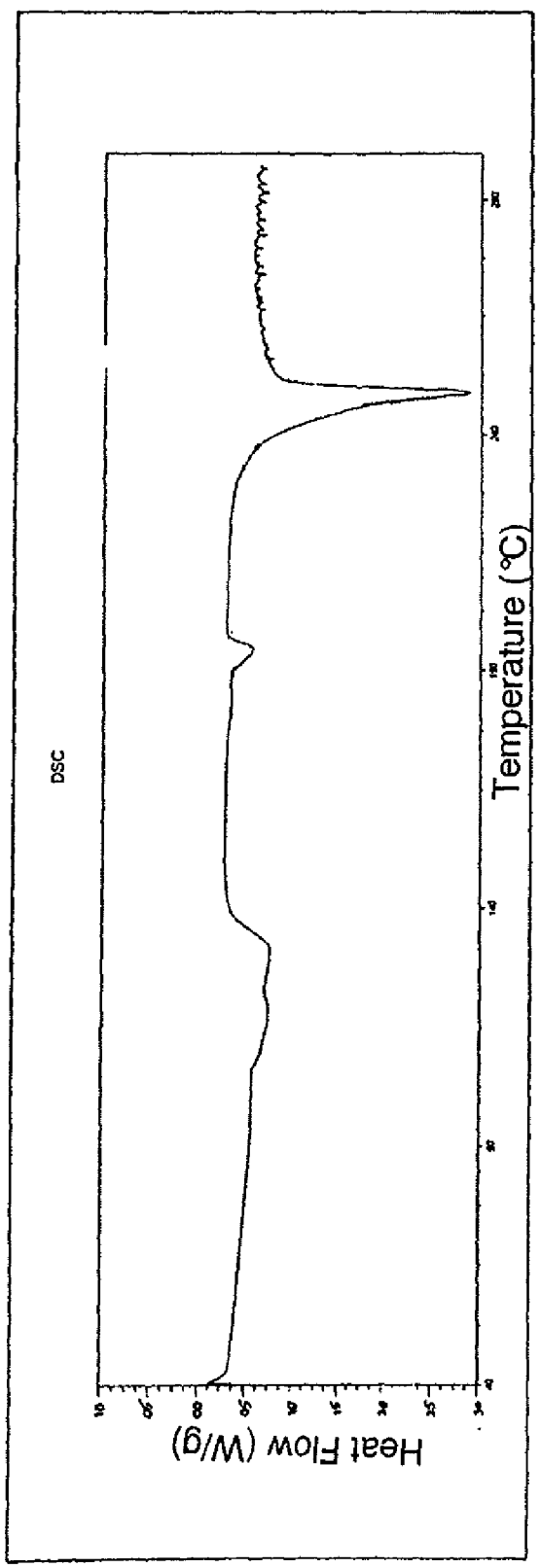
FIG. 19 shows an illustrative example of differential scanning calorimetry thermogram of crystalline Form B of pemetrexed prepared according to Example 10.

Also provided is crystalline Form B of pemetrexed diacid having XRPD pattern characteristic peaks approximately at: 5.7, 12.1, 12.3, 17.7, 18.4, 20.2, 22.2, 22.5, 22.7, 24.7, 25.6, 25.8, 26.6, 28.2, 30.3, 31.3, and 31.8, ±0.2 degrees 2θ. Crystalline Form B of pemetrexed diacid having XRPD pattern substantially in accordance with FIG. 16 is separately contemplated. Pemetrexed diacid crystalline Form B of the present invention has a characteristic thermogravimetric (TGA) curve corresponding to a weight loss of about 5% w/w, and is shown in FIG. 17. Pemetrexed diacid crystalline Form B may be further characterized by an infrared absorption spectrum in potassium bromide having characteristic absorption peaks at about 3424, 3310, 3190, 2941, 2354, 1694, 1524, 1374, 1087, 945, 776, and 662, ±5 cm$^{-1}$. Pemetrexed diacid crystalline Form B with infrared spectra substantially in accordance with FIG. 18 is separately contemplated. Pemetrexed diacid crystalline Form B is further characterized by its DSC thermogram, which is shown in FIG. 19, having endothermic peaks at about 114, 134, 195, and 249° C.

The process for preparing pemetrexed diacid crystalline Form B includes reacting 4-[2-(2-amino-4,7-dihydro-4-oxo-1H-pyrrolo[2,3-d]pyrimidin-5-yl)ethyl]benzoic acid methyl ester with aqueous sodium hydroxide solution, and subsequently neutralized with an acid up to a pH about 3 in the presence of a Isopropyl alcohol followed by drying by conventional method as described in the specification earlier. Acid utilized for neutralization may be selected from hydrochloric acid, hydrobromic acid, sulfuric acid, acetic acid, p-toluene sulfuric acid, and the like. Suitable temperature for conducting the reaction may range from about 20° C. to about 80° C. The dried product can optionally be milled to get a desired particle size. Milling or micronization can be performed prior to drying, or after the completion of drying of the product. The milling operation reduces the size of particles and increases surface area of particles by colliding particles with each other at high velocities. Milling can be done suitably using jet milling equipment like an air jet mill, or using other conventional milling equipment.

In yet another embodiment, there is provided a pharmaceutical composition comprising the amorphous pemetrexed disodium or amorphous solid dispersion of pemetrexed disodium with at least one pharmaceutically acceptable carrier or polymorphs of pemetrexed diacid or its pharmaceutically acceptable salts produced by the processes of the present invention with at least one pharmaceutically acceptable excipient.

Amorphous pemetrexed disodium or amorphous solid dispersion of pemetrexed disodium with at least one pharmaceutically acceptable carrier or Polymorphs of pemetrexed or its pharmaceutically acceptable salts obtained by processes of the present invention can be formulated as solid compositions for oral administration in the form of capsules, tablets, pills, powders or granules. In these compositions, the active product according to the invention is mixed with one or more pharmaceutically acceptable excipients. The drug substance can be formulated as liquid compositions for oral administration including for example solutions, suspensions, syrups, elixirs and emulsions, containing inert diluents solvents or vehicles such as water, sorbitol, glycerine, propylene glycol or liquid paraffin, may be used.

The compositions for parenteral administration can be suspensions, emulsions or aqueous or non-aqueous, sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients that are of use in the present invention include but are not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, polyvinyl pyrrolidone, hydroxypropyl cellulose, hydroxypropyl methyl cellulose, pregelatinized starch and the like; disintegrants such as starch, sodium starch glycolate, pregelatinized starch, crospovidone, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, complex forming agents such as various grades of cyclodextrins, resins; release rate controlling agents such as hydroxypropyl cellulose, hydroxymethyl cellulose, hydroxypropyl methyl cellulose, ethyl cellulose, methyl cellulose, various grades of methyl methacrylates, waxes and the like. Other pharmaceutically acceptable excipients that are of use include but not limited to film formers, plasticizers, colorants, flavoring agents, sweeteners, viscosity enhancers, preservatives, antioxidants and the like.

Having described the invention with reference to certain specific aspects and embodiments, other embodiments will become apparent to one skilled in the art from consideration of the specification. The invention is further defined by reference to the following examples describing in greater detail certain specific aspects and embodiments, the examples not being intended to limit the scope of the invention in any manner. It will be apparent to those skilled in the art that many modifications, both to materials and methods, may be practiced without departing from the scope of the invention.

EXAMPLES

Example 1

Preparation of Amorphous Pemetrexed Disodium Using Spray Drier (Using Water and Methanol in the Ratio of 7.4:92.6)

Pemetrexed disodium (5 g) was dissolved in the solvent mixture of methanol (240 ml) and demenaralized water (19 ml) at a temperature of 25 to 35° C. and then filtered the solution, followed by washing with methanol (10 ml). Total amount of solution was evaporated completely until dryness using spray dryer parameters:
Inlet Temperature: 75° C.
Pump: 20%
Aspirator: 50%
$N_2$ pressure: 5 Kg/cm$^2$
to get the dried title compound.
Yield: 1.7 g.
TGA: 8.268% weight loss.

The obtained sample kept in a sealed polythene bag at a temperature of 20° C. to 25° C. for a period of 58 days to check the physical stability. The material was found to retain its amorphous nature after 58 days of holding at ambient room temperature, as indicated by retention of the original XRPD pattern.
Water content: 11.51% by Karl Fisher method.
XRPD and physical observation after 58 days—Amorphous Example 2

Preparation of Amorphous Pemetrexed Disodium (Using Water and Methanol in the Ratio of 6.9:93.1)

Pemetrexed disodium (3 g) was dissolved in methanol (100 ml) followed by demenaralized water (10 ml) was charged. Methanol (20 ml) and demenaralized water (1 ml) were charged to the obtained suspension and then the suspension was heated to a temperature of 55° C. Methanol (20 ml) was added to the suspension. The solution was filtered and washed with methanol (10 ml). The obtained total filtrate was evaporated completely using spray drier using spray dryer parameters:
Inlet temperature: 100° C.
Pump: 20%
Aspirator: 70%
$N_2$ pressure: 5 Kg/cm$^2$
to get the title compound.
Yield: 0.7 g
TGA: 9.81% weight loss.

Example 3

Preparation of Amorphous Pemetrexed Disodium by Reducing the Methanol Quantity (Using Water and Methanol in the Ratio of 50:50)

Pemetrexed disodium (5 g) was dissolved in demenaralized water (35 ml). Methanol (35 ml) was added to the solution and then filtered. The obtained filtrate was subjected to spray drying drier using spray dryer parameters:
Inlet temperature: 100° C.
Pump: 10% (3 ml/minute)
Aspirator: 70%
$N_2$ pressure: 5 Kg/cm$^2$
followed by vacuum drying at a temperature of 45° C. to get the title amorphous material.
Yield: 1.8 g
Water content: 6.09% by KF method The obtained sample kept in a sealed polythene bag at a temperature of 20 to 25° C. for a period of 7 days to check the physical stability. The material was found to retain its amorphous form after 7 days of holding, as indicated by retention of the original XRPD pattern.

Example 4

Preparation of Amorphous Pemetrexed Disodium (Using Water and Methanol in the Ratio 37.2:68.8)

Pemetrexed disodium (20 g) was dissolved in demenaralized water (140 ml). Methanol (280 ml) was added to the obtained solution at a temperature of 25 to 35° C. and filtered the solution followed by washing with methanol (30 ml). The obtained total filtrate was subjected to evaporation until dryness using spray drier to obtain title compound.

Yield: 11.14 g

Water content: 6.49% by KF method

The obtained sample kept in a sealed polythene bag at a temperature of 20 to 25° C. for a period of 3 days to check the physical stability. The material was found to retain its polymorphic form after 3 days of holding, as indicated by retention of the original XRPD pattern.

The sample was kept in a petri dish and stored at room temperature for a period of 24 hours to check the physical stability. The material was found to retain its polymorphic form after 24 hours of holding, as indicated by maintenance of the original XRPD pattern.

Example 5

Preparation of Amorphous Solid Dispersion of Pemetrexed Disodium with Povidone K-30

Pemetrexed disodium (2.5 g), Povidone (Grade K-30; 2.5 g) and demineralized water (35 ml) were charged into a flask and stirred the whole mixture for 5 minutes. Methanol (70 ml) was added to the obtained suspension at a temperature of 30° C. and stirred for 15 minutes. The suspension was filtered and washed with methanol (10 ml). The obtained total filtrate was subjected to spray drying at a temperature of 100° C. for a period of 1 hour using Spray dryer parameters:

Inlet temperature: 100° C.

$N_2$ pressure: 5 kg/cm$^2$

Aspirator: 70%

Pump: 20% to get titled amorphous solid dispersion of Pemetrexed Disodium with Povidone K-30

Yield: 2 g

Water content: 7.51 wt % by KF.

Example 6

Preparation of Amorphous Solid Dispersion of Pemetrexed Disodium with HPMC

HPMC (2.5 g) was suspended into demineralized water (17.5 ml). Pemetrexed disodium (2.5 g), demineralized water (17.5 ml), methanol (60 ml) were added to the obtained suspension at a temperature of 28° C. and stirred the whole solution for a period of 25 minutes. The obtained solution was filtered and washed with methanol (10 ml). The resultant filtrate was evaporated using spray drier at a temperature of 100° C. for a period of 30 minutes using Spray drier parameters:

Inlet: 100° C.

$N_2$: 5 kg/cm$^2$

Aspirator: 70%

Pump: 20% to get the titled dispersion of Pemetrexed Disodium with HPMC.

Water content: 7.67 wt % by KF.

Example 7

Preparation of Pemetrexed Disodium (Using Freeze Drying Process)

Pemetrexed disodium (1.0 g) was dissolved in water (7.5 ml) and the solution was taken into a freeze dryer at about 24° C. The resultant solution was subjected to freeze drying at −15° C. for about 15 hours, leaving a solid after completion of the freeze-drying. The solid was collected to afford 880 mg of the title compound.

TGA weight loss: 20.88%

Example 8

Preparation of Mixture of Amorphous and Crystalline Form III of Pemetrexed Disodium by Azeotrophic Distillation Pemetrexed disodium (1.0 g) was dissolved in water (7 ml) and the resultant solution was charged into a Buchi Rotavapor. Toluene (50 ml) was charged followed by azeotropic distillation of water at about 103° C. The distillation step was repeated 8 times to afford 800 mg of the title compound.

TGA weight loss: 21.94%

% Crystallinity=22.1 wt %

Example 9

Preparation of Pemetrexed Crystalline Form A

Sodium hydroxide (6.91 g) was dissolved in water (172.8) and then the solution was charged into a round bottom flask under a nitrogen atmosphere. Dimethyl N-[4-(2-{4-hydroxy-6-aminopyrrolo-[2,3-d]pyrimidin-3-yl}ethyl)benzoyl]-L-glutamic acid PTSA salt (25 g) was charged into the flask. The reaction mixture was stirred for 1 hour and then diluted with ethanol (172.8 ml. The reaction mixture was subjected to pH adjustment to 3.05 with 1N HCl (20 ml) at 27° C. The reaction mixture was heated to 70° C. and stirred for 10 minutes, then was allowed to cool to 27° C. and stirred for 15 minutes. The reaction suspension was filtered and the solid washed with a mixture (150 ml) of water and ethanol (1:1 by volume). The wet solid was suction dried for 30 minutes and dried at 45° C. under vacuum of 650 mm Hg to afford 14.5 g of title compound.

TGA weight loss: 25.8%

Example 10

Preparation of Pemetrexed Crystalline Form B

Sodium hydroxide (13.8 g) was dissolved in water (345 ml) and then the solution was charged into a round bottom flask under a nitrogen atmosphere. Dimethyl N-[4-(2-{4-hydroxy-6-aminopyrrolo-[2,3-d]pyrimidin-3-yl}ethyl)benzoyl]-L-glutamic acid PTSA salt (50 g) was charged into the flask. The reaction mixture was stirred for 1 hour and then diluted with isopropyl alcohol (345 ml), and then pH adjusted to 3.01 with 1N HCl (25.8 ml). The reaction mixture was heated to 65° C. and stirred for 30 minutes, then was allowed to cool to 27° C. and stirred for 30 minutes. The reaction suspension was filtered and the solid washed with a mixture (160 ml) of water and isopropyl alcohol (1:1 by volume). The wet solid was suction dried for 30 minutes and dried at 45° C. under vacuum of 650 mm Hg to afford 31 g of the title compound.

TGA weight loss: 5.1%.

Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

What is claimed is:

1. A compound, which is an amorphous form of disodium salt of pemetrexed, having an X-ray diffraction pattern in accordance with FIG. 1.

2. The compound of claim 1, wherein said amorphous form of disodium salt of pemetrexed has water content of less than about 15% w/w.

3. The compound of claim 1, wherein said amorphous form of disodium salt of pemetrexed has water content between about 5% and about 10% w/w.

4. A composition comprising a compound of claim 1 as a solid, wherein at least 50% by weight of said solid disodium salt of pemetrexed is an amorphous form of disodium salt of pemetrexed.

5. The composition of claim 4, which is in the form of a powder suitable as active ingredient for pharmaceutical products.

6. The composition of claim 4, wherein at least 95% by weight of said solid disodium salt of pemetrexed is in the amorphous form.

7. The composition of claim 6, wherein at least 2% by weight of said solid disodium salt of pemetrexed is in the crystalline form.

8. The composition of claim 4, wherein at least 5% w/w of said solid disodium salt of pemetrexed is a crystalline form of disodium salt of pemetrexed.

9. The composition of claim 8, wherein said crystalline disodium salt of pemetrexed has an X-ray diffraction pattern, expressed in terms of 2 theta angles and obtained with a diffractometer equipped with a copper Kα-radiation source, wherein said X-ray powder diffraction pattern includes five or more peaks selected from the group consisting of peaks with 2 theta angles of 4.0±0.2, 17.3±0.2, 18.0±0.2, 19.5±0.2, 20.4±0.2, 21.0±0.2, 29.0±0.2 and 43.3±0.2 degrees.

10. The composition of claim 9, which has X-ray powder diffraction pattern substantially in accordance with FIG. 8.

11. A solid dispersion of disodium salt of pemetrexed which comprises
   i) a compound of claim 1; and
   ii) a pharmaceutically acceptable carrier, wherein the solid dispersion has a solubility in water ranging from about 50 mg/ml to about 150 mg/ml.

12. The solid dispersion of claim 11, wherein the amorphous content is equal to or greater than about 95 wt %.

13. The solid dispersion of claim 11, which is substantially free from crystalline forms of disodium pemetrexed.

14. The solid dispersion of claim 11, wherein said pharmaceutically acceptable carrier is polyvinylpyrrolidone.

15. The solid dispersion of claim 11, wherein said pharmaceutically acceptable carrier is hydroxypropylmethyl cellulose (HPMC).

16. The solid dispersion of claim 11, which comprises from about 10% to about 90% of disodium salt of pemetrexed; and from about 90% to about 10% of the carrier.

17. The solid dispersion of claim 11, which has solubility in water ranging from about 50 mg/ml to about 150 mg/ml.

18. A process for preparing the compound of claim 1 comprising:
   i) providing a solution of pemetrexed disodium in a solvent; and
   ii) removing the solvent.

19. The process of claim 18, further comprising drying the solid isolated after solvent removal.

20. The process of claim 18, wherein said solvent is an organic solvent.

21. The process of claim 18, wherein said solvent is water.

22. The process of claim 18, wherein said solvent is removed by spray drying.

23. The process of claim 22, wherein said removing step is carried out by using spray drier at an inlet temperature of about 100° C. or less.

24. The process of claim 18, wherein said solvent is isopropyl alcohol, methanol, acetone, ethyl methyl ketone, methyl isobutyl ketone, water or mixtures thereof.

25. The process of claim 18, wherein the providing step comprises dissolving disodium pemetrexed and a pharmaceutically acceptable carrier in the solvent.

26. The process of claim 25, wherein said pharmaceutically acceptable carrier is polyvinylpyrrolidone.

27. The process of claim 25, wherein said pharmaceutically acceptable carrier is hydroxypropylmethyl cellulose (HPMC).

* * * * *

UNITED STATES PATENT AND TRADEMARK OFFICE
CERTIFICATE OF CORRECTION

PATENT NO. : 8,507,508 B2
APPLICATION NO. : 12/593966
DATED : August 13, 2013
INVENTOR(S) : Raghavendracharyulu Venkata Palle et al.

It is certified that error appears in the above-identified patent and that said Letters Patent is hereby corrected as shown below:

On the Title Page:

Item (22), delete "PCT Filed: April 4, 2008" and insert --PCT Filed: April 3, 2008--;

Item (86), delete "PCT No.: PCT/US2008/059344" and insert --PCT No.: PCT/US2008/059244--.

Signed and Sealed this
Twenty-eighth Day of January, 2014

Michelle K. Lee
*Deputy Director of the United States Patent and Trademark Office*